(12) United States Patent
Hancock

(10) Patent No.: US 8,696,997 B2
(45) Date of Patent: Apr. 15, 2014

(54) HYDROXYL RADICAL PRODUCING PLASMA STERILISATION APPARATUS

(75) Inventor: Christopher Paul Hancock, Bristol (GB)

(73) Assignee: Creo Medical Limited, Wales (GB)

( * ) Notice: Subject to any disclaimer, the term of this patent is extended or adjusted under 35 U.S.C. 154(b) by 420 days.

(21) Appl. No.: 12/741,469

(22) PCT Filed: Nov. 6, 2008

(86) PCT No.: PCT/GB2008/003766
§ 371 (c)(1),
(2), (4) Date: May 5, 2010

(87) PCT Pub. No.: WO2009/060214
PCT Pub. Date: May 14, 2009

(65) Prior Publication Data
US 2010/0247403 A1  Sep. 30, 2010

(30) Foreign Application Priority Data

Nov. 6, 2007  (GB) .................................. 0721714.4
Apr. 23, 2008 (GB) .................................. 0807347.0
Sep. 17, 2008 (GB) .................................. 0816989.8

(51) Int. Cl.
*B01J 19/08* (2006.01)

(52) U.S. Cl.
USPC ................. 422/186.29; 422/186; 422/186.04; 422/22; 422/21; 118/723 MW

(58) Field of Classification Search
USPC ........... 422/186.29, 186, 186.04, 1, 4, 21, 22, 422/28; 118/723 MW
See application file for complete search history.

(56) References Cited

U.S. PATENT DOCUMENTS

| 4,207,286 | A | 6/1980 | Boucher |
| 5,111,111 | A * | 5/1992 | Stevens et al. ............ 315/111.41 |
| 5,278,519 | A * | 1/1994 | Williams ..................... 330/306 |
| 5,393,490 | A | 2/1995 | Adir |
| 6,017,414 | A | 1/2000 | Koemtzopoulos |
| 6,343,425 | B1 | 2/2002 | Sias et al. |
| 6,969,487 | B1 | 11/2005 | Sias et al. |
| 7,625,531 | B1 * | 12/2009 | Coates et al. ............. 422/186.04 |
| 8,168,128 | B2 * | 5/2012 | Seeley et al. .................. 422/186 |
| 2005/0090078 | A1 | 4/2005 | Ishihara ....................... 438/471 |
| 2007/0007257 | A1 * | 1/2007 | Uhm et al. ................ 219/121.48 |
| 2007/0144441 | A1 * | 6/2007 | Kamarehi et al. ...... 118/723 ME |
| 2007/0193517 | A1 | 8/2007 | Matsuuchi |

FOREIGN PATENT DOCUMENTS

| WO | WO 02/45756 A | 6/2002 |
| WO | WO 2006/014862 A | 2/2006 |

* cited by examiner

*Primary Examiner* — Xiuyu Tai
(74) *Attorney, Agent, or Firm* — Arent Fox LLP

(57) ABSTRACT

Sterilisation apparatus arranged controllably to generate and emit hydroxyl radicals. The apparatus includes an applicator which receives RF or microwave energy, gas and water mist in a hydroxyl radical generating region. The impedance at the hydroxyl radical generating region is controlled to be high to promote creation of an ionisation discharge which in turn generates hydroxyl radicals when water mist is present. The applicator may be a coaxial assembly or waveguide. A dynamic tuning mechanism e.g. integrated in the applicator may control the impedance at the hydroxyl radical generating region. The mist and/or gas and/or energy delivery means may be integrated with each other.

16 Claims, 26 Drawing Sheets

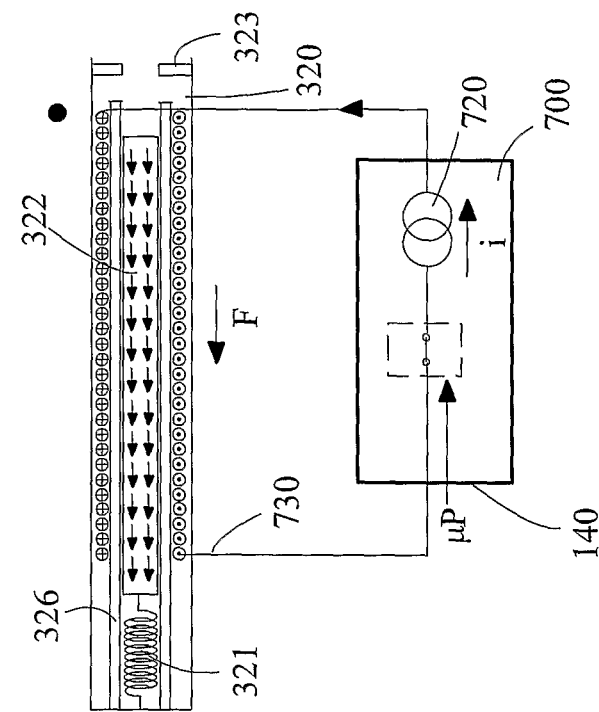
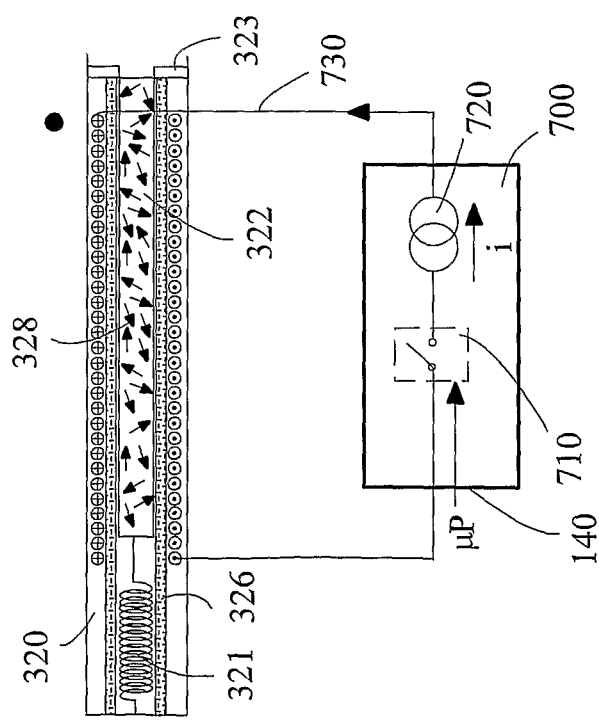

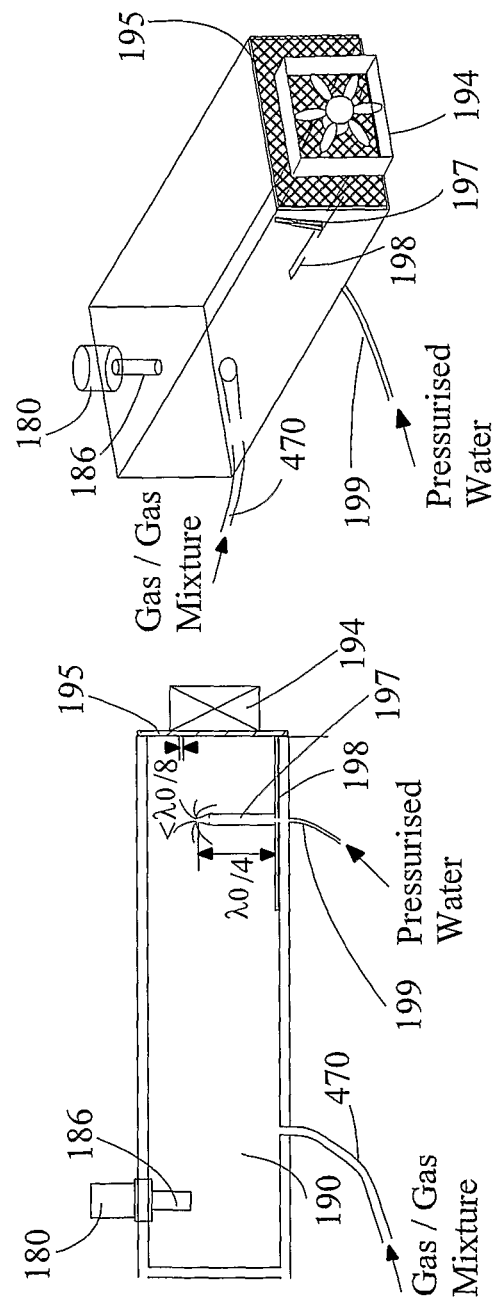

HYDROXYL RADICAL PRODUCING PLASMA STERILISATION APPARATUS

CROSS-REFERENCE TO RELATED APPLICATION

This application is a National Stage entry of International Application No. PCT/GB2008/003766 filed Nov. 6, 2008, and which claims priority to applications GB 0721714 filed Nov. 6, 2007, GB 0807347.0 filed Apr. 23, 2008, and GB 0816989.8 filed Sep. 17, 2008, the entire specification, claims and drawings of which are incorporated herewith by reference in their entirety.

FIELD OF THE INVENTION

The invention relates to sterilisation systems suitable for clinical use, e.g. on or in the human or animal body. For example, the invention may provide a system that can be used to destroy or treat certain bacteria and/or viruses associated with the human or animal biological system and/or the surrounding environment. This invention is particularly useful for sterilising or decontaminating enclosed or partially enclosed spaces, e.g. hospital bed spaces.

BACKGROUND TO THE INVENTION

Bacteria are single-celled organisms that are found almost everywhere, exist in large numbers and are capable of dividing and multiplying rapidly. Most bacteria are harmless, but there are three harmful groups; namely: cocci, spirilla, and bacilla. The cocci bacteria are round cells, the spirilla bacteria are coil-shaped cells, and the bacilli bacteria are rod-shaped. The harmful bacteria cause diseases such as tetanus and typhoid.

Viruses can only live and multiply by taking over other cells, i.e. they cannot survive on their own. Viruses cause diseases such as colds, flue, mumps and AIDS.

Fungal spores and tiny organisms called protozoa can cause illness.

Sterilisation is an act or process that destroys or eliminates all form of life, especially micro-organisms. During the process of plasma sterilisation, active agents are produced. These active agents are high intensity ultraviolet photons and free radicals, which are atoms or assemblies of atoms with chemically unpaired electrons. An attractive feature of plasma sterilisation is that it is possible to achieve sterilisation at relatively low temperatures, such as body temperature. Plasma sterilisation also has the benefit that it is safe to the operator and the patient.

Plasma typically contains charged electrons and ions as well as chemically active species, such as ozone, nitrous oxides, and hydroxyl radicals. Hydroxyl radicals are far more effective at oxidizing pollutants in the air than ozone and are several times more germicidal and fungicidal than chlorine, which makes them a very interesting candidate for destroying bacteria or viruses and for performing effective decontamination of objects contained within enclosed spaces, e.g. objects or items associated with a hospital environment.

OH radicals held within a "macromolecule" of water (fog drop) are stable for several seconds and they are 1000 times more effective than conventional disinfectants at comparable concentrations.

A recent article[1] considers the use of OH radicals produced by strong ionisation discharges to eliminate microbial contamination. In this study, the sterilisation effect on *E. coli* and *B. subtilis* is considered. The bacteria suspension with a concentration of $10^7$ cfu/ml (cfu=colony forming unit) was prepared and a micropipette was used to transfer 10 µl of the bacteria in fluid form onto 12 mm×12 mm sterile stainless steel plates. The bacteria fluid was spread evenly on the plates and allowed to dry for 90 minutes. The plates were then put into a sterile glass dish and OH radicals with a constant concentration were sprayed onto the plates. The outcomes from this experimental study were:

1. OH radicals can be used to cause irreversible damage to cells and ultimately kill them;
2. The threshold potential for eliminating micro-organisms is ten thousandths of the disinfectants used at home or abroad;
3. The biochemical reaction with OH is a free radical reaction and the biochemical reaction time for eliminating micro-organisms is about 1 second, which meets the need for rapid elimination of microbial contamination, and the lethal time is about one thousandth of that for current domestic and international disinfectants;
4. The lethal density of OH is about one thousandths of the spray density for other disinfectants—this will be helpful for eliminating microbial contamination efficiently and rapidly in large spaces, e.g. bed-space areas; and
5. The OH mist or fog drops oxidize the bacteria into $CO_2$, $H_2O$ and micro-inorganic salts. The remaining OH will also decompose into $H_2O$ and $O_2$, thus this method will eliminate microbial contamination without pollution.

[1] Bai et al, "Experimental studies on elimination of microbial contamination by hydroxyl radicals produced by strong ionisation discharge", *Plasma Science and Technology*, vol. 10, no. 4, August 2008

SUMMARY OF THE INVENTION

At its most general, the invention provides a sterilisation system arranged controllably to generate and emit hydroxyl radicals.

According to the invention, there may be provided sterilisation apparatus comprising an applicator having a hydroxyl radical generating region and an outlet for directing generated hydroxyl radicals out of the hydroxyl radical generating region towards a region to be sterilised; an enclosure for confining the hydroxyl radicals in the region to be sterilised; a power generator connected to deliver energy into the hydroxyl radical generating region; and a mist generator connected to deliver water mist (which may also mean moisture or fog) into the hydroxyl radical generating region, wherein the apparatus is configured to create a high impedance at the hydroxyl radical generating region when water mist and energy are delivered thereto thereby to create an ionisation discharge for generating hydroxyl radicals for delivery out of the applicator or device.

This system may be used to produce OH radicals for applications relating to hospital ward or bed space or operating theatre decontamination or sterilisation.

The apparatus may include a coaxial assembly having an inner conductor surrounded by and separated from an outer conductor, wherein the inner conductor tapers at its distal end to concentrate an electric field in the hydroxyl radical generating region to promote ionisation discharge when water mist and microwave energy are delivered thereto. The inner (centre) conductor may be part of a coaxial impedance transforming network arranged to generate a high enough electric field to enable a useful non-thermal plasma to be struck or an ionisation discharge to take place.

The apparatus may include a gas feed connected to deliver gas into the hydroxyl radical generating region, wherein the created ionisation discharge is a plasma of the gas. The plasma may be combined with the mist to produce OH radicals with a concentration that is suitable to decontaminate a range of isolated regions or spaces defined by a flexible or portable enclosure that can be filled with the radicals produced by the applicator or device. The enclosure enables the OH radicals to be concentrated and prevents the whole ward being flooded with OH radicals.

The mist generator may include a valve contained within the inner conductor of the coaxial assembly, the valve having an outlet located to deliver mist at the distal end of the inner conductor. The valve may be a needle valve. The needle valve may be operated mechanically, as in the case of an air brush arrangement, or electronically as in the case of a fuel injection system, to enable the water (or other fluid) to be introduced into the centre conductor under pressure.

A nozzle may be included at the distal end of the conductor (needle valve) to act as an atomiser to enable a controllable mist to be produced. The valve used to control the flow of water (or other fluid) along the centre conductor may be a solenoid valve, which is an electromechanical valve controlled by sending an electrical current through a solenoid to change the state of the valve, i.e. when the current is flowing through the winding of the solenoid, the solenoid produces a magnetic field which moves a plunger, or a rod of magnetic material, in a particular direction to open the valve and allow the flow of water along the centre conductor, and, when the current ceases, the rod may move back to a rest position, i.e. the valve is closed and the flow of water along the centre conductor is cut off.

In a particular embodiment, the valve may be connected at one end to a spring, which may be used to keep the valve closed when no field is applied and compressed to cause the valve to open when the field is applied. When the valve is open, the water (or other fluid) flows into the centre conductor and the gas (or compressed air, or gas mixture) is used to draw the water from the centre conductor to produce a mist at the nozzle. The gas also enables plasma to be produced at the distal tip of the centre conductor due to ionisation of the gas, caused by the high electric field set up at the distal tip due to the microwave or RF field and the particular antenna used, and the plasma combines with the mist to produce a concentration of OH radicals suitable for destroying a range of bacteria or viruses. When the valve is closed, the water (or other fluid) is unable to flow along the centre conductor, but the gas (or compressed air, or gas mixture) is still able to produce a plasma due to ionisation of the gas (or compressed air, or gas mixture) caused by the high electric field set up at the distal tip due to the microwave field produced by the generator and the particular antenna or resonator structure used. This plasma may also be used to destroy a range of bacteria or viruses.

If the applicator is set up to produce plasma and OH radicals through controlled mist generated inside the centre conductor, the gas inlet may be positioned downstream of the valve used to control the flow of water along the centre conductor. In certain instances it may be preferable for the applicator to use a mechanical valve arrangement. In this instance, the mechanical valve mechanism, the means of creating an E-field high enough to ionise the gas (or mixture of gases), the supply of water and the compressed gas (or mixture of compressed gases) are integrated into a handheld device. The device may take the form of a pen and may be used to sterilise a number of objects used in a clinical environment or a range of surfaces. The compressed gas (or gas mixture) may come from an air compressor and/or a gas cylinder(s) and is introduced into the applicator using a suitable connection tube. The connections to the centre conductor that act as inlets for the water supply and the compressed gas (or gas mixture) must be such that the electromagnetic field set up inside the applicator structure is unaltered. This may require the feed tube to be made from a low loss dielectric material or it may be necessary to set-up the feed lines as an arrangement of tuning stubs. In this particular arrangement, a mechanical valve is included to control the flow of the compressed gas (or gas mixture) and to introduce the water into the centre conductor. Upon actuation of a button or trigger, a needle valve releases a flow of water and simultaneously releases a flow of compressed gas into the system. The compressed gas draws water from the distal end of the centre conductor and the water molecules are atomised, due to the inclusion of a suitable nozzle, as the water exits the centre conductor. In operation, the user may depress a button located on the outer body of the applicator when it is desired to produce the OH radicals. It is preferable for the solenoid valve to be contained within the applicator as the valve should release the water, which may be under pressure, straight into the centre conductor (needle) to enable a mist to be instantaneously produced at the distal end of the applicator, which will combine with the plasma to produce OH radicals.

Although it is preferable for the system to contain the valve in the applicator, this invention is not limited to this arrangement, i.e. the valve control may be contained within the instrument containing the microwave generator and associated control electronics. It may be preferable for the water to be fed using a gravity fed mechanism rather than a pump.

Water may be introduced into the system downstream of the gas supply in order to use the gas to withdraw or assist with the withdrawal of the water from the centre conductor. In this particular arrangement, the valve assembly will be changed to allow the gas to flow past the valve, i.e. the valve and seal arrangement will be reconfigured.

It may also be preferable for the gas (or gas mix) to be directly combined with the water rather than having the two separated. Where the water supply and the gas supply (or mixture) is separated, it is preferable for the gas (or gas mixture) to be fed into the centre conductor downstream from the water supply, i.e. closer to the distal tip. This is because the applicator is able to produce plasma or OH radicals in accordance with the state of the needle valve, i.e. if the valve is open OH will be created and if the valve is closed plasma will be created. This enables the applicator, or instrument, to be used in a range of applications relating to the human or animal body and external environments. For example, it may be used to kill or destroy prions existing on the surface of surgical instruments.

In an alternative arrangement, the applicator may comprise a waveguide cavity containing the hydroxyl radical generating region, the waveguide cavity having a coupler or launcher located therein for delivering microwave energy from the microwave radiation generator to the hydroxyl radical generating region, and a mist inlet for delivering fog, moisture or mist into hydroxyl radical generating region. In a particular embodiment, the microwave energy generating device may be directly connected to the waveguide cavity where the OH radicals are created.

An antenna (e.g. dipole antenna) may be located in the waveguide cavity to concentrate an electric field in the hydroxyl radical generating region to promote ionisation discharge when water mist and microwave energy are delivered thereto. The mist inlet may be a passageway through the antenna.

The waveguide cavity may include an impedance adjustor arranged to control the impedance at the hydroxyl radical generating region when water mist and microwave energy are delivered thereto. The impedance adjustor may be arranged to selectively occupy either (i) a strike state in which a first impedance for creating the ionisation discharge is exhibited at the hydroxyl radical generating region when water mist and microwave energy are delivered thereto, or (ii) a maintenance state in which a second impedance for maintaining the ionisation discharge is created at the hydroxyl radical generating region when water mist and microwave energy are delivered thereto, the second impedance being lower than the first impedance. The ionisation discharge may be created repeatedly (or plasma may be struck repeatedly) by pulsing the energy from the microwave generator. In this particular instance, only one impedance state may be required.

The microwave energy may be delivered to the waveguide cavity via a feed line, and wherein the impedance adjustor may comprise either (a) a stub tuner having one or more stubs that are adjustably insertable into the feed line; (b) a stub tuner having one or more stubs that are adjustably insertable into the waveguide cavity; or (c) one or more fixed stubs connected in shunt to the feed line that are electronically switchable between an open circuit configuration and a short circuit configuration; or (d) one or more variable capacitors connected in series and/or parallel to the feed line.

The mist generator comprises a ultrasonic fog generator.

The system may comprise a controllable microwave or RF power generator or plurality of generators; a controllable supply of gas (or gas mixture); a controllable supply of mist or fog; a single or plurality of applicators that produce suitable plasma and/or suitable concentrations of OH radicals: a cable assembly or means of transferring the microwave or RF power from the generator(s) into the applicator(s); an enclosure to enable suitable concentrations of OH radicals to be built up or established; a control system to control the operation of the microwave (or RF) generator, the gas flow and mixing system, and the mist or fog generator; a means of introducing the applicator(s) into the space or enclosure where decontamination or sterilisation is to be performed; a user interface to enable the user to control the plasma or OH radical sterilisation, decontamination or cleaning system, and a means of monitoring the OH concentration and the effectiveness of the cleaning process (this may be an external process or instrument).

The apparatus may use an integrated applicator (in which the mist and plasma is generated) or may use a separate first applicator to produce the plasma and a separate second applicator to produce the mist or fog. In the latter arrangement, the mist or applicator is then coupled to the plasma applicator using an abutment arrangement to enable the mist to be effectively coupled to the plasma to enable OH radicals of suitable concentration to be generated. The OH radicals are introduced into an enclosed environment and the environment is filled with a concentration of radicals suitable for killing bacteria or contaminants that exist inside the enclosed section. A plurality of integrated or separate component applicators may be used to introduce the OH radicals into the enclosed environment at a number of ports arranged around the periphery of the enclosure. The device used to create the ionisation discharge and the device to create the mist may be separate units or sub-assemblies and the two units may be placed in two different locations within the flexible enclosure. The instrumentation containing the microwave generator, the gas (or mixture of gases), the mist generator, the control system and the user interface is preferably located outside the enclosed environment to enable the user to control the system without being exposed to high concentrations of OH radicals.

The enclosure may be a portable arrangement that can be moved around inside a hospital, e.g. the enclosure may take the form of a large umbrella or a tent or a large balloon. The purpose of the enclosure it to contain and confine the hydroxyl radicals therein. This may serve both to protect an external environment from unwanted effects and to concentrate the hydroxyl radicals in the region to be sterilised. It is highly desirable for the enclosure easily transportable without being damaged. It may be desirable for the enclosure to be moved around in a hospital ward from one bed-space to the next to perform a serial decontamination process without the need to close the hospital ward, thus reduce downtime or create additional resources for treating or caring for patients, therefore the enclosure should ideally be suitable to enclose an area containing a bed, a bed side cabinet and any other bed space furniture that may be present in the area. It may be preferable for the flexible enclosure to be double skinned or consist of a plurality of walls, skins or membranes in order to ensure that as many OH radicals as possible are contained within the enclosed space and that a high concentration of OH radicals can be maintained.

The lifetime of OH radicals in air may be 1 to 3 seconds. If the enclosure is portable, there may in use be gaps at the interface between its edges and the edges of the region to be sterilised. To prevent OH radical escaping, the surface of the enclosure, especially at the edges, may be coated with a material that acts as a good absorber of OH radicals.

Alternatively or additionally, the enclosure may seal the region to be sterilised. The seal may be effected by attachment elements, or, for parts of the enclosure which contact a floor surface, weighted elements (e.g. containing sand or the like) that promote good contact between the enclosure and floor. Instead of a physical seal, the OH radicals may be confined in the enclosure by a back pressure generated at the edges therefore, e.g. acting to directly gas moving out of the enclosure back into the enclosure.

One or more fans may be provided to distribute the air containing OH radical within the space in the enclosure. The fan(s) may be located inside the enclosure.

The OH radicals produced by this system may oxidise the bacteria contained within the bed space into $CO_2$, $H_2O$ and micro inorganic salts. The remaining OH radicals may decompose into $H_2O$ and $O_2$ and so the system should eliminate microbial contamination without pollution—this is of particular significance in the intended application since patients and healthcare workers will be present during the decontamination process, i.e. a patient may be located in a bed either side of the space where decontamination is taking place during the time this process is taking place. The fact that harmful by products may not be produced by the sterilisation process means that it may not be necessary to totally seal off the bed space area being decontaminated, i.e. it may not be necessary to put sealing tape around the edges of the enclosure where the closure comes into contact with the floor and it is not necessary to use air tight seals around the input ports where the OH radicals are introduced into the enclosure. This is also beneficial in terms of decontamination time, i.e. the portable enclosure can be moved from one bed space to the next in a matter of minutes.

However, it may also be beneficial to concentrate the OH radical in an enclosed region to ensure 100% bacteria or bug kill rate, and it may be undesirable to have OH radicals continuously filling spaces where patients or staff are present. The system presented herein may create high densities of OH radicals in a controllable manner to kill all bacteria or viruses or bugs in a partially enclosed region where no harm can be caused to patients or staff that are present in regions nearby the partial enclosure or positioned elsewhere within the hospital ward.

The flexible structure means that the enclosure may be moved and set up by a single member of hospital staff. The generator or instrumentation may be located on the top of a small trolley or contained within a bespoke enclosure with wheels, thus this sterilisation process is not resource intensive. Once the bed space has been decontaminated, the patient can be put straight back into bed with the assurance that the OH radical system has totally decontaminated the area where he/she is going to be located; this should provide a high level of patient comfort and peace of mind.

The instrumentation used to generate the OH radical supply (including gas bottle(s) and water cylinder) may be housed in an enclosure with wheels so that it can be moved from bed to bed or ward to ward. The portable enclosure may be made from a fabric material or a plastic sheet with metal struts to give it support, i.e. a similar arrangement to a camping tent or an umbrella may be used.

The apparatus may include a means of recycling the OH radicals and/or the gas (or mixture of gases) back into the system to increase the efficiency of operation in terms of minimising gas and electrical energy used and reducing the introduction of stray OH radicals into spaces around the enclosure where patients or staff may be present. The system for recycling the OH radicals may consist of an arrangement comprising: one or two chambers, a first pump (motor) to remove OH radicals from the system, a second pump (motor) to reintroduce radicals back into the enclosure or into the applicator and an arrangement of pipes or tubes. The system may also include an arrangement of one way valves. It may be preferable to use a plurality of outlet and inlet pipes to ensure that the radicals are evenly or uniformly circulated or distributed within the enclosure. The system may also contain a fan or an arrangement of fans to ensure that the radicals inside the enclosure are moved around within the decontamination space to ensure that all bacteria within the space is successfully destroyed. Where the gas is extracted and fed back into the applicator, a Y-type combiner may be used to recombine the recycled gas with the gas (or gas mix) produced by the cylinder(s). The ionisation discharge may be created using air or compressed air; in this instance a compressed air generator may be used to replace the gas cylinder(s).

This arrangement may also be used to feed the gas (or gas mixture) back into the applicator(s) to produce more plasma to enable new radicals to be generated. In this arrangement, the gas (or gas mixture) that gets pumped back into the chamber is pumped back out and fed into the applicator or stored in a separate chamber ready for use. The recycled gas and the gas from the main cylinder(s) is/are then combined using a Y-type gas connector or the like. This will reduce the demand on the external gas supply.

The apparatus may include a means of measuring the spectral content (wavelength and magnitude) of the energy produced by the system at the distal end of the applicator where the plasma/OH is emitted. The measurement system may comprise an arrangement of photodiodes or light detectors and associated signal conditioning, and the information from the diodes may be fed into the microprocessor or control system to enable the wavelength and the intensity of the UV and plasma produced at the output of the system to be controlled. Photodiodes are semiconductor light sensors that generate a current or voltage when the P-N junction in the semiconductor is illuminated with light.

The intensity and wavelength information may be fed back into the system to enable adjustments of microwave power level, gas flow rate and gas mixture to be made in order to optimise the generation of the OH radicals. Particular devices that may be used to implement the detectors include: Si photodiodes, Si PIN diodes, multi-element type Si photodiodes and Si avalanche photodiodes (APDs). It may be preferable to integrate a mini spectrometer arrangement into the applicator or the output of the system to provide the function of wavelength and intensity measurement. In such arrangements, the following types of sensors may be used: CCD sensors, CMOS linear sensors and InGaAs sensors. A particular device that may be considered is a C10082MD or C10083MD mini-spectrometer from Hamamatsu, which employs a CMOS linear image sensor as the detector.

These devices can be used to measure light intensity within the UV and the near IR range of wavelengths. A range of sensors may be employed to enable light intensity measurements to be made within the 200 nm to 2200 nm wavelength range.

For the system introduced here, it may be preferable to use a polychromator type arrangement whereby a grating is used as the wavelength dispersing element and an array type detector is placed along the focal plane of the focussing lens. Polychromators are designed to allow simultaneous detection of multiple spectra, which could be advantageous for use in our system.

The impedance adjustor may be arranged as a dynamically controlled or statically controlled matching network or tuner to enable the microwave energy used to create the plasma to be impedance matched into the high impedance state required to strike the plasma and the low impedance state required to sustain or maintain the plasma. Alternatively, a fixed tuning arrangement may be provided that enables an ionisation discharge to occur on the leading edge of each pulse of microwave power. Such an arrangement will ensure that the microwave power generating device, i.e. a magnetron, is protected from damage due to frequently occurring gross impedance mismatches during the plasma strike or ionisation discharge occurrence, i.e. the output impedance of the magnetron will be matched to the impedance that is set up within the cavity when ionisation discharges or plasma strikes occur. It may be preferable to operate the system in pulsed mode.

The system may also include a means of measuring wavelength and intensity of the plasma/UV/OH produced at the output of the system (the applicator) and this information may be used in a feedback loop to control the wavelength and intensity of the energy produced by the system.

In the current invention, the power level may be adjustable in a controlled manner, e.g. the microwave energy can be modulated in a controlled manner using at least one modulator or means of modulation.

The invention also draws upon the availability of moisture that may be produced either through the environment where the plasma is being generated (applications within the body) or by introducing moisture or fog or mist into the applicator through external means, e.g. fog produced by an ultrasonic transducer and a vessel of water. The introduction of fog or mist or moisture may be used to enable hydroxyl radicals to be produced, which are known to be effective for killing bacteria or fungi.

The apparatus may include means for delivering the generated OH radicals into an open space or a flexible or portable enclosure where they are used to sterilise or decontaminate the space contained within the enclosure. In this particular arrangement, the OH radicals generated inside the waveguide cavity may be blown through the cavity using a first fan (or plurality of fans) and then pumped out of the waveguide cavity using a pump or a second fan (or plurality of fans), e.g. a first fan is connected to the input wall of the waveguide cavity and a second extraction fan is connected to the output wall of the waveguide. It may be preferable to use only one fan connected at the input end to blow the radicals through the cavity or it may be preferable to channel a portion of the radicals produced at the output back to the input end in order to prevent large quantities of air being blown into the waveguide cavity, which may have a detrimental effect on the OH radicals produced at the output of the waveguide cavity. In such an arrangement, microwave energy may be coupled into the cavity using an E-field or an H-field probe and the ionisation discharge required to create the OH radicals may be created using a dipole antenna arrangement made up of a quarter wavelength monopole and a quarter wavelength return, placed inside the waveguide cavity at a region where the E-field is a maximum in order to assist the breakdown process, and/or a tuning arrangement, e.g. a stub tuner, may be used to set-up a suitable impedance or microwave field to enable the ionisation discharge to occur. The dipole arrangement may consist of a metallic rod with a sharp point at the distal end, that has a length equal to a quarter of the wavelength at the frequency of operation, connected to the centre of a flat disk that has a diameter equal to half the wavelength at the frequency of interest, and located inside the waveguide cavity to create the necessary ionisation discharge. In this particular arrangement, both the rod and the disk are preferably made from a material that has a high conductivity, i.e. copper or brass. The mist or fog required to create the OH radical may be provided by an ultrasonic transducer placed inside a vessel containing water (or covered by a continuous supply of water). This arrangement may be placed inside the waveguide cavity at a location close to where the ionisation discharge is taking place or may be connected externally to one of the waveguide walls, where a hole has been made and a wire mesh or grid or arrangement of holes or an arrangement of slots is used to allow the fog to enter the waveguide cavity, but not allow microwave energy to be radiated through the hole. Alternatively the mist may be generated by feeding a supply of pressurised water through a hollow channel formed in the centre of the quarter wavelength monopole (described above). A nozzle may also be included at the end to enable a supply of atomised water molecules to emanate from the end of the centre conductor to create the desired mist, which can then be instantly turned into OH radicals as soon as the ionisation breakdown or discharge occurs at the tip of the same nozzle where the mist is being generated.

If a magnetron is used as the microwave source, its output (normally a E-field antenna) may be coupled directly into the waveguide cavity.

As mentioned above, a gas (or a mixture of gases) may be introduced into the waveguide cavity to assist in the ionisation discharge process and create energy at the most appropriate wavelength to enable the OH radicals to be generated when this energy is coupled with the mist or fog present inside the waveguide. It may be preferable to use the gas (or gas mixture) used to create the ionisation discharge (or the plasma) to also push water through the centre of the monopole or to assist in creating the mist.

The monopole may be replaced with an electrode that has a pointed end, or spike. The electrode may be positioned opposite one of the tuning stubs such that the tip of the electrode and the end of the tuning stub are in close proximity. The tip of the electrode and the tip of the particular tuning stub may be pointed and made from a material that can withstand high temperatures, e.g. tungsten. In this arrangement, the tuning stubs should be set such that the E-field generated in this region is a maximum to enable the electrode to assist in the ionisation discharge process.

In the implementation of this particular aspect of the current invention it may be preferable to use a microwave oven cavity to provide the field required to cause the ionisation breakdown necessary to generate the OH radical concentration, e.g. an industrial size microwave oven that can produce microwave power levels in excess of 1 kW may be used. It may also be preferable to partially pressurise the cavity in order to reduce the breakdown voltage required to create the ionisation discharges.

The dipole may be replaced with an alternative structure suitable to create the ionisation discharges or high intensity UV, e.g. a vacuum tube may be placed inside the cavity or the cavity walls may be reduced in certain locations within the waveguide cavity or an electrode with a point or spike on the end may be introduced to create the necessary ionisation discharges.

In this specification microwave frequency may be used broadly to indicate the range 400 MHz to 100 GHz, but preferably the range 1 GHz to 60 GHz. Specific microwave frequencies that have been considered are: 900 MHz, 2.45 GHz, 3.3 GHz, 5.2 GHz, 10 GHz, 14.5 GHz and 24 GHz. RF frequency may be used broadly to indicate the range 50 kHz to 500 MHz. Specific RF frequencies that may be of interest are 100 kHz, 500 kHz, 13 MHz, 27.12 MHz, 40.68 MHz, 50 MHz and 100 MHz.

Other independent aspects of the invention may include the applicators discussed herein and methods of generating OH radicals for sterilisation.

BRIEF DESCRIPTION OF THE DRAWINGS

Features of the invention are now explained in the detailed description of examples of the invention given below with reference to the accompanying drawings, in which:

FIGS. 7(a), 7(b) and 7(c) are schematic views of a needle valve comprising a solenoid;

FIGS. 25(*a*) and 25(*b*) are views of a fifth plasma applicator according to yet another embodiment of the invention.

DETAILED DESCRIPTION

Further Options and Preferences

Figure 1:
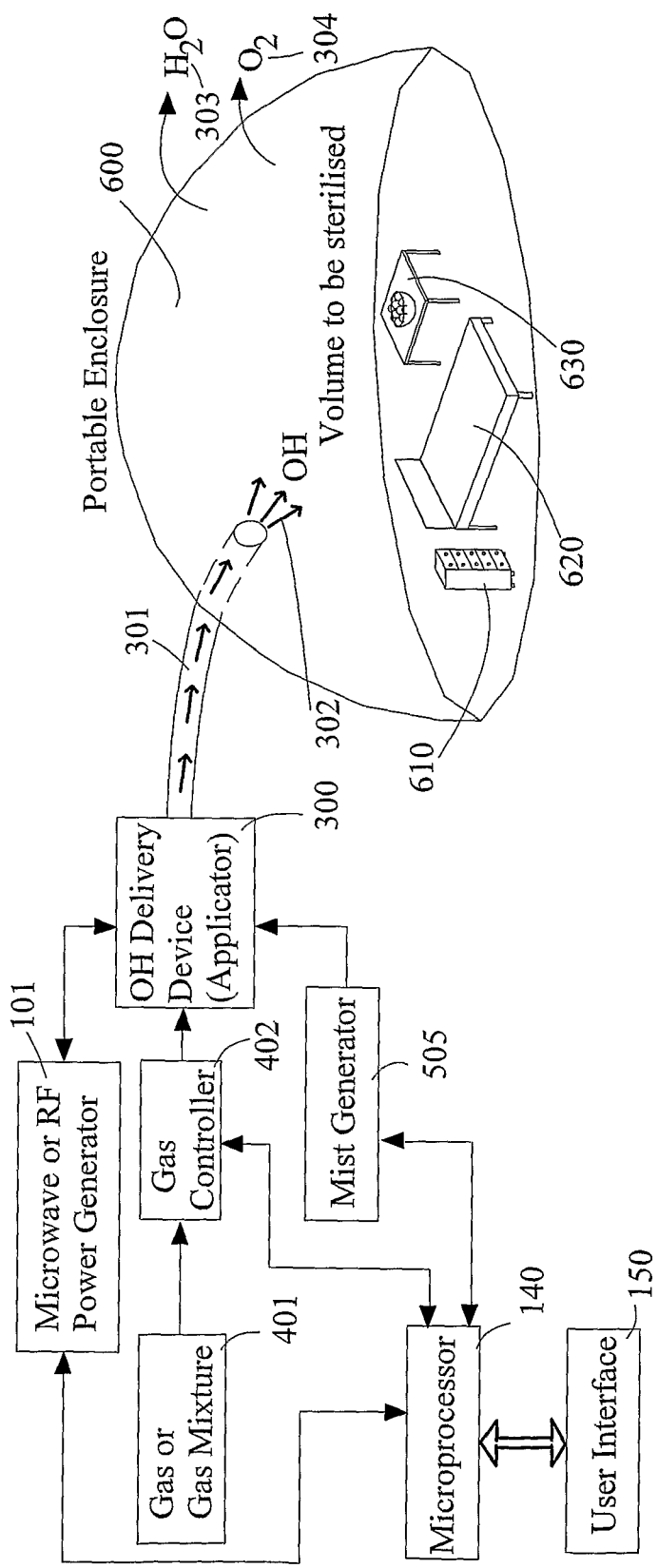
FIG. 1 is a schematic diagram of a sterilisation system for producing hydroxyl radicals that is an embodiment of the invention.

This invention relates to a system and method of generating hydroxyl radicals in a range of concentrations to kill bacteria or contaminants associated with hospital environments, outpatient surgeries or other areas where is it required to perform safe and effective decontamination. The invention may also be used to kill bacteria or bugs that exist within carpets or other flooring materials in hospitals, offices or domestic homes.

The system introduced here uses a combination of microwave or RF energy, a gas (or gas mixture) and a mist (or moisture) generator to produce a controllable supply of OH radicals that have a high enough concentration to be useful to perform effective decontamination of enclosed spaces. In this invention, the enclosed space may be defined by a portable or flexible enclosure, which may be an integral part of the system.

Since OH radicals are efficient sterilisation agents, the decontamination process may have a short duration, e.g. only a few minutes. It may therefore be possible to decontaminate large areas, e.g. complete hospital wards containing up to 50 bed space areas, in short periods of time.

The invention may also provide applicator structures which make use of the skin effect at microwave frequencies to enable a hollow conductor (or needle) to constitute the final transformer section of an impedance multiplier structure or a single coaxial structure that produces a high enough microwave field to generate plasma when combined with an appropriate gas (or gas mixture). In more detail, the use of energy at microwave frequencies (e.g. 2.45 GHz) to produce the plasma allows the wall of the conductor used to form the centre conductor of the final impedance transformer within the applicator structure to be kept thin due to the fact that the thickness of conductor required to enable the microwave field to propagate along the conductor is proportional to the inverse of the frequency of the microwave energy. For this reason, when skin depth is shallow, a solid conductor can be replaced by a hollow tube with no loss in microwave performance. Skin depth can be calculated using $$\delta s = \sqrt{\frac{2}{\omega \mu \sigma}}, \text{ or}$$

$$\delta s = \sqrt{\frac{\rho}{\pi f \mu}},$$

where $\delta s$ is skin depth (m), $\omega$ is radian frequency (Hz), $\sigma$ is conductivity (S), $\rho$ is resistivity ($\Omega$m), f is frequency (Hz), $\mu$ is permeability of free space (H/m), i.e. $4\pi \times 10^{-7}$ H/m, and $\pi$ is 3.1415927.

For small diameter structures, it is necessary to use energy at microwave frequencies if the outer wall thickness is made sufficiently small.

The percentage of power transferred as a function of material thickness can be expressed as $$\% P = \frac{1 - e^{-x}}{\delta s} \times 100,$$

where x is the thickness of the layer of metallization (m), and % P is the percentage of the power flowing in given thickness of metallization (W). This equation predicts that for a thickness of metallization of six skin depths, 99.75% of the power will be transported.

At the frequency of interest and for the centre conductor materials of interest, the required wall thickness will be in the order of 5 µm to 100 µm, but is not limited to this range, thus this enables the centre conductor to be hollow to allow water to be driven through it under pressure to form the required mist at the end. The actual wall thickness will also be dependent upon the conductivity of the material used to implement the final conductor (or the centre conductor of the coaxial line if the structure consists of only one centre conductor, i.e. no impedance transformations take place within the structure) used to create the required field. A further advantage of using high microwave frequency energy is that the wavelengths involved makes it possible to practically implement a plurality of quarter wavelength impedance transformer sections inside a sensible size applicator structure, i.e. at 2.45 GHz the quarter wavelength is 30.6 mm and at 24 GHz is 3.125 mm. It may be preferable to use a material that can withstand high temperatures when implementing the final conductor within the applicator or the final transformer section, e.g. tungsten rod or wire may be used. For lengths in excess of 20 mm the tungsten may be plated or coated with a material that is a good electrical conductor, i.e. silver or copper, to reduce the losses. The coating process may take the form of an electroplating process, i.e. using silver nitrate to coat the tungsten rod with silver.

The hollow section may contain a needle valve, which may be a solenoid valve or a mechanical arrangement, to enable a mist or fog to be produced at the distal end of the conductor (or needle), where the plasma is formed to combine with the plasma to produce OH radicals of appropriate density or concentration to be useful for disinfecting decontaminating a number of external and internal environments. The needle may contain a nozzle to enable atomisation of the water molecules to take place. The applicator may also use a single impedance coaxial or waveguide structure along with an adjustable impedance matching or tuning mechanism or system to enable the high and low impedance states to be set up inside the applicator where the plasma and OH radicals are generated. The applicator may be a coaxial structure or waveguide (loaded or unloaded) structure.

The system may also contain an arrangement of photodiodes within the distal end of the final conductor or waveguide section of the applicator to enable the wavelength and the amplitude of the plasma/UV spectrum to be monitored. This information may be fed back to the generator control system to enable adjustments of microwave or RF power level, modulation frequency and/or gas flow rate/mixture to be made to ensure that optimal plasma and/or OH radical concentration are produced. A calorimeter may also be contained within the applicator to measure the energy being produced at the output of the system.

The OH radicals may also be generated inside a microwave waveguide cavity. In this embodiment, the system may comprise a control system and a waveguide cavity containing an E-field or H-field probe to introduce the microwave energy into the cavity, an antenna (or other structure) placed inside the cavity and/or an arrangement of tuning elements to assist with the ionisation breakdown process, a gas (or a mixture of gases) to also assist the ionisation discharge process, and a mist or fog generator to enable suitable concentrations of OH radicals to be produced.

For example, a metallic rod with a point at its distal end that has a length equal to a quarter of the wavelength at the frequency of interest may be connected to the centre of a disk with a diameter equal to half the wavelength at the frequency of interest may be used to form the dipole antenna and located inside the waveguide cavity to create the discharge. In this arrangement, both the rod and disk are preferably made from a material that has a good conductivity, i.e. copper, brass, silver or gold. It may be preferable to use tungsten that has been plated with these materials.

The system may include a pump or fan arranged to expel OH radicals generated inside a waveguide cavity out through an outlet in the waveguide cavity. For example, a first fan may be employed to blow the radicals through the cavity and a second extraction fan may be employed to pull the radicals out of the cavity and into the space requiring decontamination. A portion of the OH radicals produced in the cavity may be recycled, e.g. brought back to the input.

Pressurised water may be fed into the system (e.g. suction fed). In one example the gas feed may be arranged to draw the water along the centre conductor to create the mist. Alternatively, gravity fed water supply may be used.

The applicator may include an ultrasonic fog generator arranged to create mist inside the applicator or at its distal end. The ultrasonic fog generator may comprise an ultrasonic transducer set up to vibrate ultrasonically near the distal end of the applicator, where the transducer is covered with a flow of liquid, e.g. water, to enable a fog to be created, which will combine with the plasma to create a supply of OH radicals at the tip of the centre conductor. Where water or mist is introduced through an opening in the cavity, a wire mesh or grid may be placed over the opening to prevent energy from escaping. The size of the apertures or slots that make up the mesh should be equal to or less than one eighth of the wavelength at the frequency of operation in order to prevent microwave energy from being radiated out of the waveguide cavity.

A microwave oven may be used to produce the field required to cause the ionisation breakdown required to generate the OH radical concentration, e.g. an industrial size microwave oven may be adapted and used that can produce microwave power levels up to and in excess of 1 kW. The waveguide cavity may be pressurised to reduce the breakdown voltage required to create the ionisation discharge.

The radiation source may be a microwave energy source or an RF energy source, e.g. operating at 50 MHz or 10 MHz. In this instance, a single impedance coaxial assembly may be used within the applicator to create the necessary E-field to cause the ionisation discharge with the preferred gas (or gas mix). A single impedance section would be used here due to the fact that it would be impractical to use quarter wavelength transformer sections, i.e. a quarter wavelength transformer at an operating frequency of 10 MHz is 7.5 metres long. In this arrangement, it may be necessary to include an automatic matching network at the output of the RF generator or within the applicator in order to create the high impedance (high voltage) condition necessary to cause the initial ionisation discharge followed by the low impedance condition necessary to maintain the plasma. This matching network would contain lumped elements, i.e. physical inductors and capacitors rather than distributed elements that are used to describe co-axial and waveguide structures.

The system may contain an impedance matching mechanism to match the microwave or RF energy into the plasma to ensure that the plasma is efficiently struck and maintained, but the invention is not limited to using such a mechanism.

The microwave or RF source may take the form of a solid state transistor based generator, a magnetron, a travelling tube, a klystron or the like, depending upon the level of microwave or RF power required, which itself is dependent upon the concentration of OH radicals and the sterilisation volume or the required space to be decontaminated, e.g. a volume of $1\ m^3$ or more. It may be necessary to set up an array of 100 plasma sources with 100 applicators emitting plasma or OH radicals, where 100 W of microwave or RF power is required to generate the plasma from each source; in this instance a 10 kW generator will be required. In such an arrangement, controllable mist or moisture or fog may be coupled into each individual plasma source at or near the plasma plume to enable the OH radicals to be produced.

Gases that may be used in the invention include: air, helium, argon, nitrogen, compressed air, and carbon dioxide, but this invention is not limited to using these particular gases. This invention is not limited to using only one inert gas, for example, various concentration of argon, air and helium may be used, i.e. 1% air and 99% helium.

FIG. 1 shows an embodiment of the system, which comprises of a controllable microwave or RF power generator 101, which may contain a solid state amplifier that makes use of the following microwave/RF device technologies: LDMOS, BJT, IGBT, MOSFET, GaAs or GaN. The requisite microwave power level required to produce a high enough density of OH radicals within the enclosed volume may also be achieved using the following tube or resonant cavity based technologies: magnetron, travelling wave tube, Klystron (reflex Klystron, two-cavity Klystron, multicavity Klystron), backward wave oscillator, Gyrotron, Klystrode/Inductive Output Tube (IOT), or the like as the means of producing the required output power.

The microwave/RF power generator also contains control and protection components and may include a tuning mechanism to enable high impedance and low impedance states to be automatically set up in accordance with the plasma condition, and a microwave circulator with a power dump load to protect the amplifier against damage due to high levels of reflected power that may come back due to an impedance mismatch at the applicator or elsewhere within the microwave line-up between the output port of the circulator to the input port of the applicator. Full details of the microwave power generator are given later in this description.

A suitable gas (or mixture of gases) 401 is fed into gas controller 402, which is used to control the flow rate and mixture of gases introduced into OH delivery applicator 300 based on control signals provided by microprocessor 140. It may be preferable to use Argon (Ar) as the gas used to create the plasma since Ar could also be used to flush out the system and is already used and available in hospitals.

A mist generator 505 is also shown connected to OH delivery applicator 300 and controlled by microprocessor 140. The mist generator may comprise of a water supply and a water pump (this will be described in more detail later in the description), or an ultrasonic transducer.

Microprocessor 140 is used to control the microwave power generator 100, the gas controller 402 and the mist generator 505. The microprocessor may take the form of a single board computer, a microcontroller, a digital signal processor, or a combination of these devices. It may be preferable for a second microprocessor to be included in the system to act as a watchdog to monitor the state of the first (main) microprocessor to ensure it is operating correctly. A user interface 150 is connected to microprocessor 140 and is used to enable the user to input information into the system and to display or output information to the user.

User interface 150 may take the form of a touch screen display, a membrane keypad or an arrangement of push switches or buttons and an LED or LCD display, or the like.

OH delivery applicator 300 takes in the microwave power produced by generator 100, the gas (or gas mixture) from gas controller 402 and the mist (or pressurised water) from mist generator 505 and produces a supply of hydroxyl radicals. More specific details relating to the design of OH applicator 300 is provided later in this description. The supply of OH radicals is channelled through a delivery mechanism 301 into a portable enclosure 600. The delivery mechanism or delivery channel 301 may be a flexible pipe or tube that can be coupled to the wall of the portable enclosure 600 without leakage or loss of OH radicals 302. The portable enclosure 600 may be a flexible tent, an umbrella or a similar arrangement that can be set up to enclose the space or volume where sterilisation is required. Portable enclosure 600 and delivery channel 301 may be manufactured using a flexible plastic or fabric. The enclosure 600 may comprise a plurality of walls or skins in order to minimise the risk of losing OH radicals due to damage to the enclosure when it is moved around in the hospital or through general wear and tear during use. The enclosure 600 and channel 301 may be combined to form a disposable item or may be reusable. In the arrangement shown in FIG. 1, the volume or space being sterilised contains a set of drawers 610, a bed 620 and a bedside table 630 to represent a typical set of items contained within the bed space occupied by a patient in a typical hospital ward. FIG. 1 also shows the inside of enclosure 600 flooded with OH radicals 302, which are used to sterilise or decontaminate the floor, the drawers 610, the bed 620 and the table 630. If OH radicals escape due to gaps or air between the base of portable enclosure 600 and the floor or due to small holes or tears in the fabric used to form enclosure 600 this should not present any risk to patients occupying adjacent bed space due to the fact that the OH radicals that do not oxidise the bacteria into carbon dioxide ($CO_2$), water ($H_2O$) and micro organic salts will decompose into $H_2O$ (303) and $O_2$ (304).

An arrangement of fans or an air blower inside the enclosure may be arranged to move the OH radicals around so as to ensure that the complete space and objects contained within it are decontaminated and all bacteria is destroyed. Alternatively or additionally, a plurality of ports may be located around the periphery of the flexible enclosure to introduce the OH radicals into the enclosure.

It may be preferable for portable enclosure 600 to be a double walled material or for it to consist of two separate walls in order to ensure that the OH radicals are confined to the space contained within the portable enclosure.

It may be preferable for the bottom of the portable enclosure 600 to be attached to the floor or another surface it is required to be attached to, i.e. walls or doors, using a method that prevents or minimises air gaps in order to ensure that the OH radicals are confined to the space contained within the portable enclosure. This method may employ adhesive tape, Velcro strips, a pocket or sand around the bottom edge or the like. It may be necessary for the enclosure to be attached to the wall or a door or a partition or the like as well as the floor of a hospital ward or similar in order to ensure that items such as pictures and radiators can be decontaminated. It may be preferable for the enclosure to cover a wall or door or partition or the like only, i.e. it is not attached to the floor at all. In these arrangements, it will be necessary to ensure that the enclosure is properly attached to the wall or the door or the partition or the like.

Figure 2:
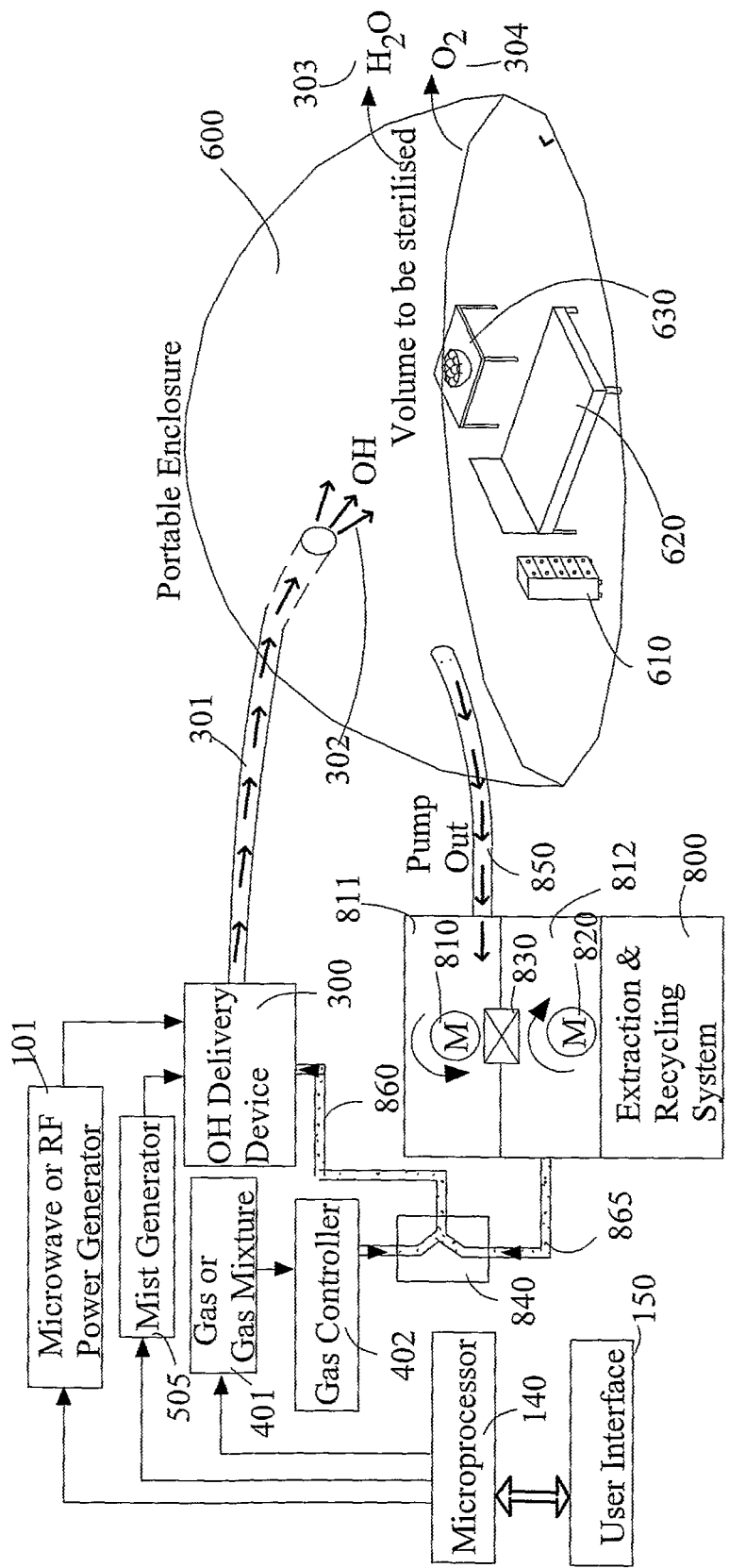
FIG. 2 is a schematic diagram of a sterilisation system for producing hydroxyl radicals having a gas extraction and recycling system.

FIG. 2 shows a similar arrangement to that given in FIG. 1, but includes a system of extracting and recycling excess gas (or gas mixture) and feeding it back into the applicator or OH delivery device 300 to assist in the production of new OH radicals. The extraction and recycling system 800 comprises of a pipe or channel or tube 850 to remove gas from portable enclosure 600, a first chamber 811, first pump 810, a valve 830, a second chamber 812, a second pump 820, a tube 865 to extract gas from second chamber 812 and transport it to gas combiner 840, a tube to transfer gas from gas controller 402 to gas combiner 840, and a tube 860 to transfer gas from gas combiner 840 into OH delivery device 300 to enable new OH radicals to be generated. The two chambers 811 812, pumps 810, 820 and valve 830 may be replaced by a single chamber (811 or 812) and a single pump (810 or 820). The advantage of using two separate chambers (with one way valve 830 and pumps 810, 820) may be to allow time for the OH radicals to be transformed back into a gas and reach a stable state prior to being recycled or being transferred back into the system to create new OH radicals.

Figure 3:
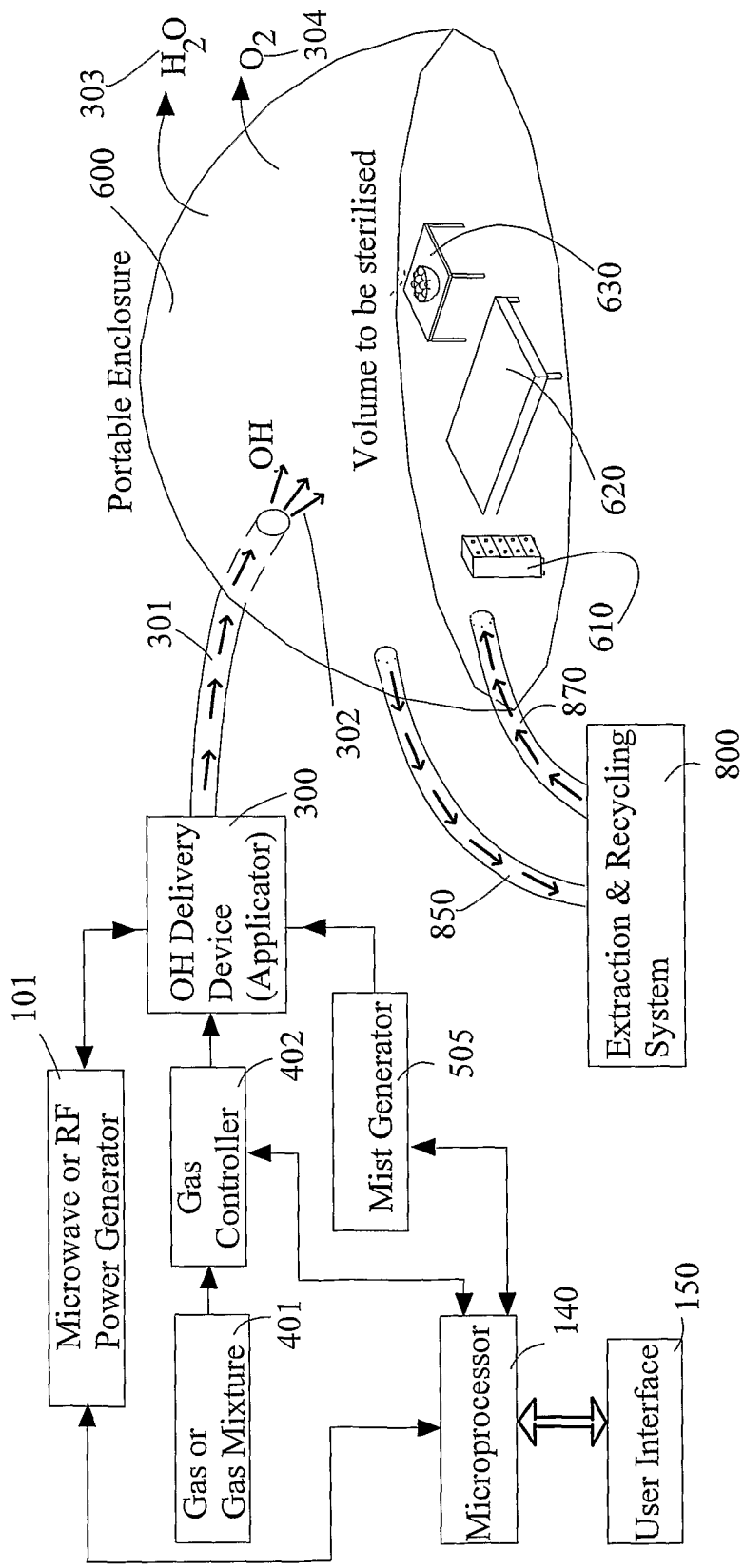
FIG. 3 is a schematic diagram of another sterilisation system for producing hydroxyl radicals having a gas extraction and recycling system.

FIG. 3 shows an arrangement similar to that given in FIG. 1, but where the OH radicals are extracted and recycled directly, i.e. the gas is not extracted and fed back into the applicator to create new OH radicals, but the OH radicals are extracted using first tube or pipe 850, fed into extraction and recycling system 800 and pumped straight back into portable enclosure 600 through second tube or pipe 870. It is necessary for the extraction and recycling process to happen in a time frame that is shorter than the lifetime of the OH radical in order to ensure that the OH radical has not been converted into another form, i.e. $O_2$ or $H_2O$, before the recycling process has been completed.

Figure 4:
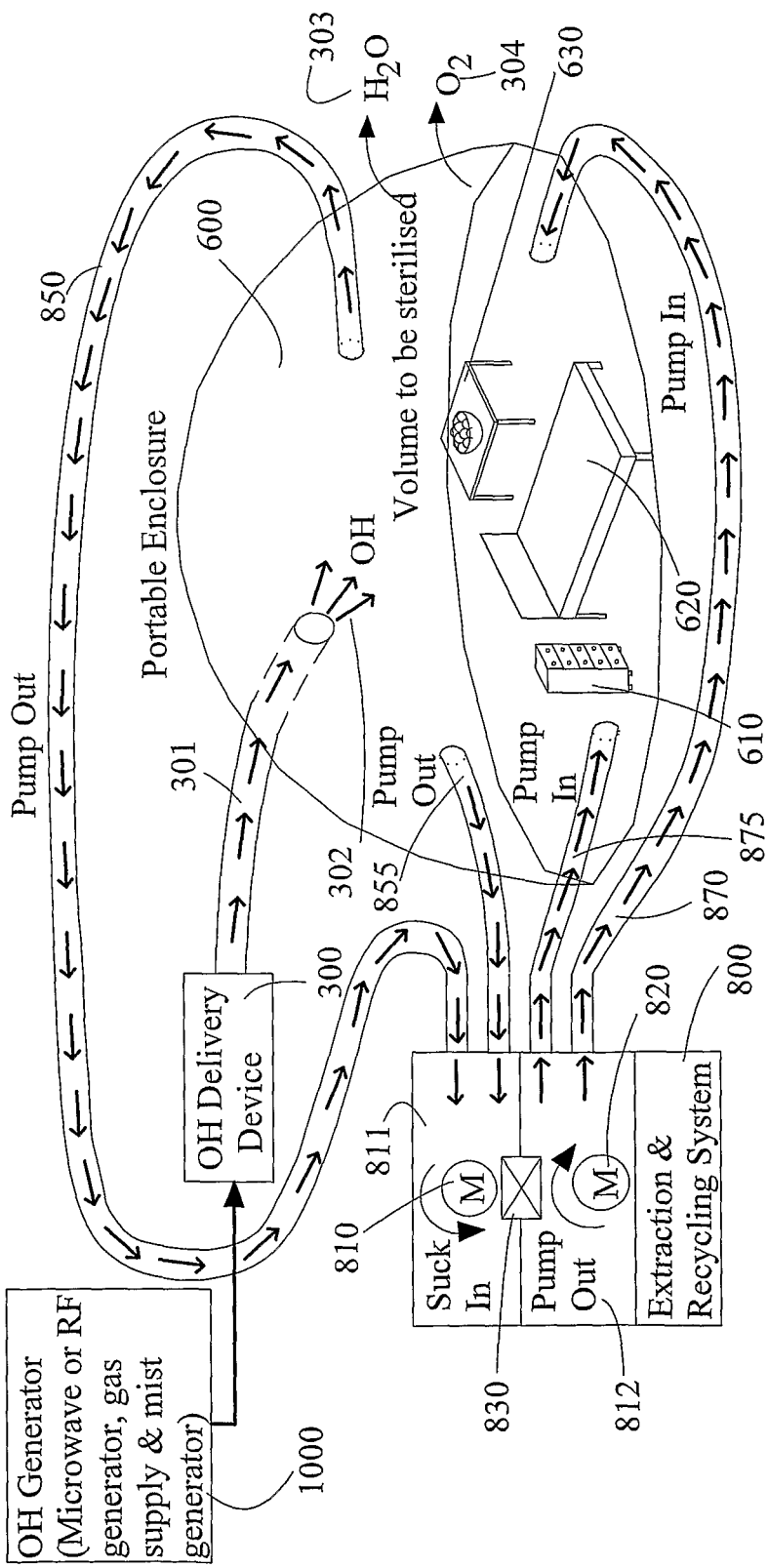
FIG. 4 is a schematic diagram of yet another sterilisation system for producing hydroxyl radicals having a gas extraction and recycling system.

FIG. 4 shows a similar system for extracting and recycling the OH radicals, but where two tubes 850, 855 are used to suck radicals out of portable enclosure 600 and two tubes 870, 875 are used to transfer OH radicals back into portable enclosure 600. Extraction and recycling system 800 comprises first chamber 811 to hold OH radicals, first pump 810 to suck radicals in, valve 830 to transfer OH radicals from first chamber 811 into second chamber 812, second chamber 812 to hold or store OH radicals and second pump 820 to pump OH radicals out of second chamber 812 back into portable chamber 600 via OH transport pipes 870, 875. In this arrangement, the microwave generator, the gas supply system and the mist generator have been integrated into a single unit—OH generator 1000.

Figure 5:
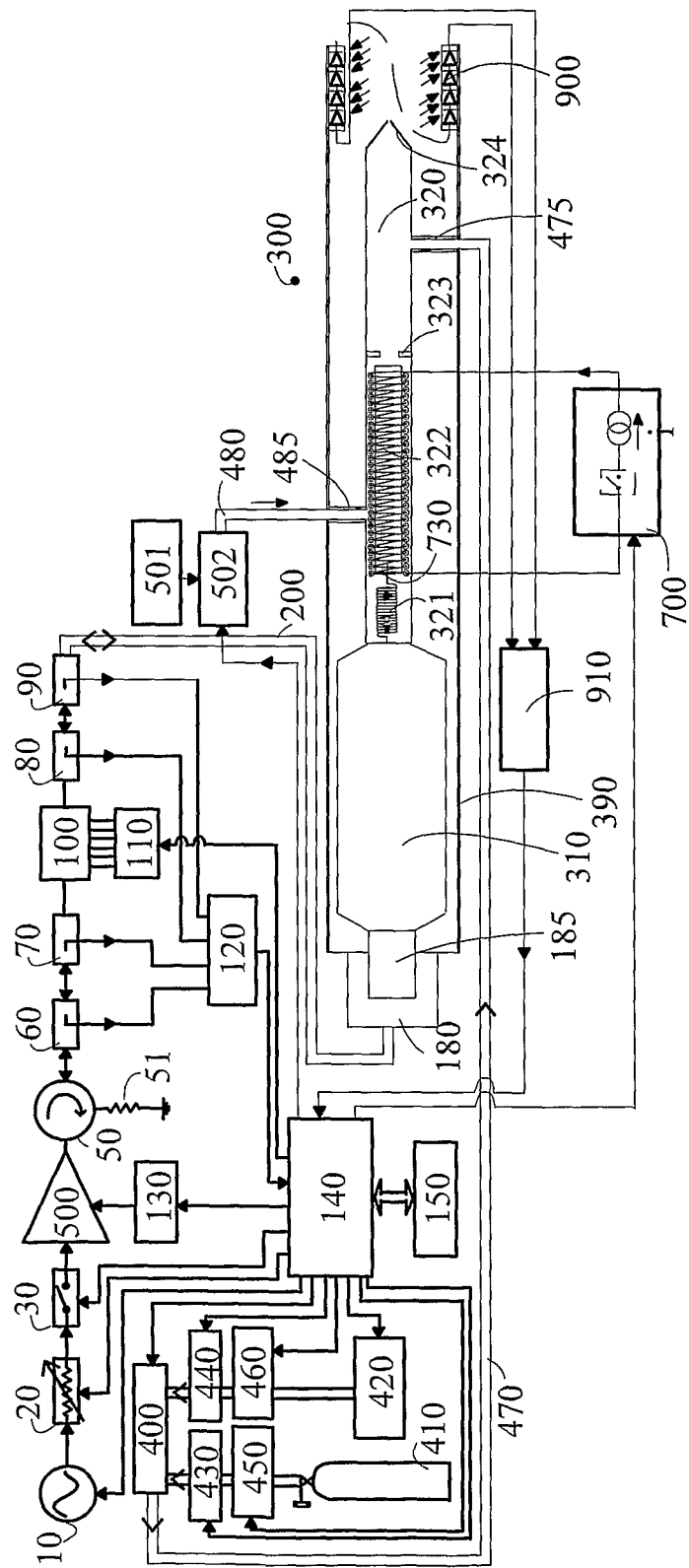
FIG. 5 is a schematic diagram of another sterilisation system for producing hydroxyl radicals having an automatic tuning mechanism integrated in a plasma applicator.

FIG. 5 provides a more detailed diagram of microwave power generator 101, gas (or gas mixture)/gas controller 401/402, mist generator 505, and OH delivery device 300. In the particular arrangement shown in FIG. 5, a dynamic tuning mechanism is used to ensure that the high impedance plasma strike and the low impedance plasma maintain conditions can be automatically set up to ensure an efficient plasma is generated.

Considering FIG. 5 in more detail, the source of microwave energy 10 is preferably a low power microwave source oscillator, i.e. a device that is able to produce power levels from greater than −10 dBm to less than 20 dBm, that produces a well controlled single frequency, but where this single frequency may be adjustable over a narrow band of frequencies, i.e. has a centre frequency of 2.45 GHz, which is adjustable between 2.44 GHz and 2.46 GHz. The source oscillator 10 may be a voltage controlled oscillator (VCO), a dielectric resonator oscillator (DRO), a Gunn diode oscillator or a similar device that is capable of producing a controllable low power microwave signal. A frequency synthesiser that comprises of a plurality of VCOs or DROs may also be used. It should be noted that if a tube or resonant cavity power generating device is to be employed in a particular embodiment then it may not be necessary to include source oscillator 10.

The output from the source oscillator 10 is connected to the input port of a power level controller 20, whose function is to enable the power level of the signal from source oscillator 10 to be adjusted over a range that is suitable to enable the plasma to be struck and then enable the plasma energy to be adjusted. This in turn may control the number of OH radicals produced by the system. The power level controller 20 may be a PIN diode attenuator that may be a reflective or absorptive type. The output from the power level controller 20 is connected to the input of a first modulator 30, whose function is to switch the microwave power produced at the output of power controller 200N and OFF (or modulate) using a signal produced by microprocessor 140 to enable the output microwave power produced at the output of power amplifier 500 to be in a pulsed format rather than a continuous wave format. The ability to control the switching action of first modulator 30 enables the pulse ON time, the pulse OFF time and the pulse format to be controlled (modulation). This enables the ratio between the ON and OFF times (the duty cycle) and the frequency (the inverse of the sum of the ON time and the OFF times) to be determined. The modulation scheme employed here may not necessarily be periodic, i.e. it may consist of a train of pulses with various duty cycles and frequencies. The ability to control the pulse ON and OFF times in this manner provides an additional means of controlling the energy produced by the plasma and the number or density of OH radicals produced by the system.

The output from first modulator 30 is fed into the input of the power amplifier 500. Power amplifier 500 is preferably a semiconductor based amplifier whose function is to amplify the power level at the output of first modulator 30 to a level that is sufficient to enable a plasma to be struck and to enable enough energy to be delivered into the plasma for the plasma to produce a useful clinical effect in terms of reducing or killing bacteria or viruses and for the plasma to be combined with a mist to enable OH radicals to be produced with a high enough concentration to enable effective decontamination or sterilisation of an external environment, or an enclosed environment, to take place. Power amplifier 500 may comprise of a plurality of stages, i.e. driver stage, pre-amplifier stage and high power stage. The amplifier may use following semiconductor devices: high frequency bipolar junction transistors (BJTs), heterostructure bipolar transistors (HBTs), metal oxide semiconductor field effect transistors (MOSFETs), or metal semiconductor transistors (MBSFETs). In terms of the semiconductor materials that may be used to fabricate these devices, of particular interest is gallium arsenide (GaAs) and gallium nitride (GdN). GaN FETs offer a higher efficiency (microwave output power/DC input power) when compared with GaAs FETs. This feature is of particular interest when developing a plasma system that is capable of providing high power microwave energy since the heating effects caused by the DC power losses are reduced, which increases the portability of the system and minimises the thermal design issues that need to be overcome when developing the system.

For applications relating to hospital ward or hospital space sterilisation or decontamination or other applications where a patient is not directly involved with the plasma treatment, it may be necessary to create large quantities of OH radicals or plasma. For example, to cover a section of the floor of a hospital ward, or to sterilise a mattress of a hospital bed, that may be infected with the MRSA virus or other contaminates. It may therefore be desirable to use an array of plasma applicators containing an integral mechanism for generating a mist to enable OH radicals to be generated and where the source of microwave power may be derived from a higher power microwave energy generating device such as a magnetron or a klyston, travelling wave tube (TWT), twystron (hybrid combination of a klystron driver and TWT output section in tandem in the same envelope), or a gyrotron. It is more difficult to control the level of power produced by these devices than it is when using semiconductor devices, but this may not be an issue when the plasma and/or OH radicals produced by the cleansing system is not in direct contact with patient tissue. For example, pulsed power levels in excess of 10 MW have been obtained using the twystron and multicavity klystrons. Practical embodiments may include magnetrons similar to those used in commercially available microwave ovens.

It is desirable to be able to switch the main device power supplies (drain supply in FETs and the collector supply in BJTs) OFF during periods when it is not required to produce microwave power, i.e. when the switch contact of first modulator (PIN switch) 30 is in the OFF position. A second modulator 130 may be employed to perform this function. The second modulator 130 may comprise of a plurality of lower frequency power MOSFET or BJT switches that enable the DC power supplies to be connected to the high frequency power BJTs or FETs only when it is required to generate microwave power to produce the plasma and OH radicals. The operation of the lower frequency power devices that form second modulator 130 can be controlled by varying the gate voltage or base current of the power FETS or power BJTs respectively. The control signals necessary to operate second modulator (gate-source voltages necessary to turn power FETS ON and OFF) are provided by microprocessor 140 and the signals used to control the operation of second modulator 130 may be synchronised to the control signal used to control the operation of first modulator 30. Second modulator 130 may have a slower response time than that of first modulator 30, therefore, it may be desirable to modulate or pulse using first modulator 30 inside a time window when second modulator 130 is enabled or switched ON. For example, second modulator 130 may be switched ON for a time slot of rooms and OFF for a time slot of 1 second; during the ON period, first modulator 30 may produce 50 pulses with an ON time of 1 ms and an OFF time of 1 ms, i.e. a 5o % duty cycle during the 100 ms window. First modulator 30 and second modulator 130 enable the energy produced by the plasma and OH radical generation to be controlled to ensure optimal clinical effects in terms of killing bacteria and/or viruses associated with the human or animal body and decontamination or sterilisation of hospital spaces are achieved.

The output from microwave power amplifier 500 is fed into the input port of microwave power circulator (or power isolator) 50, whose function is to ensure that high levels of reflected microwave power, due to impedance mismatches at applicator 300 or anywhere else in the path between the applicator 300 and the input port to first forward power coupler 60, cannot damage the output stage of power amplifier 500. In the arrangement shown in FIG. 5, a 50Ω power dump load 51 is shown connected to the third port of microwave power circulator 50. Any power that does get reflected back along the aforementioned path between applicator 300 and first coupler 60 will be absorbed by the power dump load 51.

The output port of the microwave power circulator 50 is connected to the main line input port of first forward power directional coupler 60, whose function is to sample a portion of the forward going power produced by power amplifier 500. This information may be used to control the level of microwave power produced by power amplifier 500 to ensure that the demanded power level is the same as the delivered power level, i.e. this information may be used in a feedback control loop to automatically adjust the input power going into the amplifier to increase the output power level in order to compensate for output power drift caused by heating or ageing of microwave components used in the line-up, or other component changes. The information provided by first forward going directional coupler 60 may also be used in the tuning algorithm to control the position of the stubs used in the matching network (or tuning filter) 100. The main line output from first forward power directional coupler 6o is connected to the main line input port of first reflected power directional coupler 70, whose function is to sample a portion of the reflected power coming back from the input port of tuning filter 100 due to an impedance mismatch caused either by the position of the tuning elements or the impedance set-up inside the tuning filter or the impedance set up within applicator 300 in accordance with the state of the plasma or OH radical concentration at the distal end of applicator 300 and the two impedance transformers within applicator 300. The information provided by first reflected power directional coupler 70 may also be used in the tuning algorithm to control the position of the stubs used in the stub tuning network (or tuning filter) 100. This information may also be used as a part of a safety mechanism to monitor the condition of the microwave components used in the line-up.

The main line output from first reflected power directional coupler 70 is connected to the input port of tuning filter 100, whose function is to set-up a condition that will enable the impedance of applicator 300 to be such that the plasma can be first struck (high impedance) and then maintained flow impedance). The condition for the plasma to be struck is a high voltage (high impedance) condition and that for it to be maintained is a high current (low impedance) condition. The tuning filter 100 may be a stub tuner that contains a single or a plurality of tuning rods or stubs, or may be an arrangement of power varactor or PIN diodes, where the bias voltage to each diode is changed to enable the capacitance to be varied. This capacitance variation is used to enable tuned conditions to be set up based on the plasma state requirements. In the system shown in FIG. 5, a stub adjuster unit 110 is included; this is associated with a mechanical tuning mechanism where tuning rods are moved in and out of a waveguide cavity, for example, a hollow rectangular or cylindrical section made out of a material with a high conductivity. Three tuning stubs are shown here, but this invention is not limited to the use of three, i.e. one, two, or four may be used. It may be preferable to employ three tuning stubs due to the fact that three stubs will enable any impedance, from open circuit to a short circuit to be set-up inside the waveguide cavity. The signals used to control the stub adjuster come from microprocessor 140, and these signals may be based on the signals produced by detection unit 120 in accordance with the information available at the coupled ports of directional couplers 60, 70, 80, and 90. The control signals provided to stub adjuster 110 may also be in the form of two fixed signal formats; a first to create a known high impedance condition that is used to strike the plasma, and a second to create a known low impedance condition to maintain the plasma. Dynamic adjustment of the tuning stubs may also be used to optimise and control the plasma energy and the OH concentration produced by the system.

Where embodiments of the current invention employ a tuning network similar to that shown in FIG. 5, it may not be necessary to include impedance transformers within applicator 300 due to the fact that tuning network 100 is able to set up any impedance. In this instance, it may be desirable to design a coaxial or waveguide applicator using standard coaxial cable or waveguide cavities that support a TEM or the dominant mode respectively.

A PID controller may be used between microprocessor 140 and stub adjuster 110 to control the response of the electro-mechanical stub adjuster 110. Alternatively, the PID control functions may be handled by microprocessor 140. A further alternative is to replace the mechanical tuning system with a power PIN or varactor diode arrangement, whereby the bias voltage applied to the diodes is used to adjust the depletion layer within the diodes to produce a capacitance variation that may be used to set up the desired high E-field and high H-field conditions at the distal end of applicator 300.

The output port of the tuning filter is connected to the main line input of second forward power directional coupler 80, whose function is to sample a portion of the forward going power coming out of tuning filter or tuning network 100. This information may be combined with the information produced at the coupled port of first forward power coupler 60 (or used independently) to control the level of microwave power produced by power amplifier 500 to ensure that the demanded power level is the same as the delivered power level, i.e. this information may be used in a feedback control loop to automatically adjust the input power level going into the amplifier to compensate for output power drift caused by heating, ageing of microwave components used in the line-up, or changes in the characteristics of tuning filter 100. The information provided by second forward going directional coupler 80 may also be used in the tuning algorithm to control the position of the stubs used in the stub tuning network (or tuning filter) 100. The main line output from second forward power directional coupler 80 is connected to the main line input port of second reflected power directional coupler 90, whose function is to sample a portion of the reflected power coming back from microwave cable assembly 200 due to an impedance mismatch caused by the impedance set up within applicator 300 in accordance with the state of the plasma or OH radical concentration produced at the distal end of applicator 300 and the two impedance transformers contained within applicator 300. The information provided by second reflected power directional coupler 90 may also be used in the tuning algorithm to control the position of the stubs used in the stub tuning network (or tuning filter) 100. This information may also be used as a part of a safety mechanism to monitor the condition of the microwave components used in the line-up, i.e. used to detect a break in the line-up or a loose connection or any other defect that may occur in the microwave line-up from the output of the measurement coupler to the distal end of applicator 300.

The main line output from second reflected power directional coupler 90 is connected to the proximal end of microwave cable assembly 200, whose function is to transport microwave energy used to strike and maintain the plasma and generate OH radical concentration from the controllable microwave generator to applicator 300. Microwave cable assembly 200, may take the form of a coaxial cable designed to support propagation of microwave energy at the frequency of interest, or any other low loss microwave energy transport structure, for example, flexible or flexible/twistable waveguide.

The distal end of microwave cable assembly 200 is connected to the proximal end of applicator 300, whose function is to take the microwave energy, the gas (or gas mixture) and the pressurised water into the device and use these them to produce plasma and OH radicals suitable for performing effective decontamination or sterilisation of bed spaces or objects or to kill bacteria/viruses associated with human or animal biological tissue. The applicator shown in FIG. 5 comprises of a first impedance transformer 390-310, a second impedance transformer 390-320, a microwave input connector 180, a means of introducing water (or pressurised water or other material) 485 into the centre region of hollow conductor 320, a means of introducing a gas (or a gas mixture or other material) 475 into the centre region of hollow conductor 320, a needle valve and actuation system to control the flow of the water (or pressurised water) a nozzle for atomising the water molecules 324, a means 900 of measuring the wavelength and intensity of the energy produced by applicator and coupling pipes or tubes 470, 480 to supply the gas (or gas mixture) and the water (or pressurised water) respectively into the overall applicator structure 300.

The sampled forward and reflected power levels (or signals) available at the coupled ports of directional couplers 60, 70, 80, and 90 are fed into detection unit 120, whose function is to condition the signals produced by the couplers to provide either amplitude or amplitude and phase information to the inputs of microprocessor 140, where this amplitude or amplitude and phase information is extracted and used to control tuning filter 100. The information from the coupled ports of directional couplers 60, 70, 80, and 90 may be routed to detection unit 120 using a four pole single throw PIN switch or a coaxial switch controlled by signals produced by microprocessor 140 to enable a single detector to be used to process the information produced by the four couplers. An arrangement of separate electronically controllable switches may also be used to achieve the same function.

The detection unit 120 may take the form of a diode detector, a homodyne detector or a heterodyne detector. Where a diode detector is used, this may take the form of a tunnel diode, a Schottky diode or any other diode that can be operated as a rectifier at the frequency of interest to provide suitable amplitude or magnitude information relating to the forward and reflected power levels available at directional couplers 60, 70, 80, or 90. The diode forms a part of a signal conditioning circuit that includes temperature drift compensation. An example of such a circuit is one that contains a thermocouple which produces a change in resistance in accordance with a change in temperature or a circuit that contains two matched diodes. The homodyne detector may take the form of a microwave mixer and a local oscillator that operates at the same frequency as the signal produced by microwave oscillator 10 to enable base band information to be extracted to provide magnitude and phase information. The heterodyne detector may take the form of at least one microwave frequency mixer and at least one local oscillator, where the local oscillator frequency is offset from the measurement (main) signal frequency. In this configuration the local oscillator frequency (ies) is (are) different from that produced by microwave oscillator 10. This arrangement may also contain band pass and low pass filters to filter out signals at unwanted frequencies contained within the intermediate frequency signal (IF) produced at the output of the microwave frequency mixer(s) and to remove signals produced at the local oscillator frequency (ies) or at the main microwave oscillator frequency 10 when they occur within the microwave line-up in locations where they are unwanted. A quadrature I-Q mixer arrangement may be employed to enable phase and magnitude information to be extracted from the base band signal.

Microprocessor unit 140 is used to control the operation of the plasma and OH radical generation system. It is responsible for controlling the operation of the following components used in the system: power level controller 20, first modulator 30, second modulator 130, gas mixer 400, flow switches 430-440, flow adjust controllers 450-460, compressed air generator 420, stub adjuster 110, water pump 502, current source 700, and the user interface 150. Microprocessor 140 also reads the signals produced by detection unit 120 and photodiode detection circuit 910 and uses this information to calculate the adjustments required to the positions of the tuning stubs, the rate of flow of the water used to create the mist, the gas mixture the flow rate, and the microwave power level and modulation format. It is desirable to determine when to introduce the gas mixture into applicator 300 in relation to the microwave energy provided by amplifier 500. It is desirable to ensure that applicator 300 is filled with gas before introducing the microwave energy into the structure in order to ensure that the plasma is struck or the ionisation discharges occur as soon as the microwave source is activated. It is also desirable to ensure that the correct or optimal conditions are set up inside the stub tuner prior to the microwave source being activated. A sequence of events that relate to the set-up and operation of the system may be as follows:

1. Set tuning stubs into a position where a known high impedance will be produced at the distal end of second conductor 320 of second impedance transformer 390-320;
2. Determine the gas flow rate, the gas mixture, and the gas pulsing sequence required to produce optimal plasma and OH radical concentration for the particular application;
3. Determine the level of microwave power and the modulation format required to produce optimal plasma and OH radical concentration for the particular application;
4. Determine water flow rate required to produce a suitable mist to enable a suitable concentration of OH radicals to be generated;
5. Introduce the gas mixture into the applicator;
6. Activate current source 700 to enable needle valve to open to allow a water mist to be created at the distal end of centre conductor 320;
7. After a period of time when it can be assured that the applicator is full of gas and a mist has been created, introduce the microwave energy into the applicator;

8. A useful concentration of OH radicals should now be available at the distal end of the applicator.

When the system is being operated in pulse mode, it may be desirable to stop the gas flow during the time that the microwave source is in the OFF state and start it again just before switching the microwave energy back on again. For example, the microwave power may be delivered using a 10% duty cycle where the ON time is 10 ms and the off time is 90 ms. In this instance, it may be desirable to start the gas flow 5 ms before the start of the microwave pulse and turn it off 5 ms after the microwave energy has been switched OFF, thus for each 10 ms of microwave energy the gas will flow for 20 ms, thus for a 10% duty cycle of microwave power, the duty cycle for the gas supply will be 20%. In this arrangement, in one time slot (or one pulse) the consumption of gas will be reduced by a factor of 5.

It may be desirable to stop the gas flow at the same time as the microwave power is turned OFF since it will take a finite time for the gas to cease flowing within the applicator.

It may also be necessary to initially start the gas flow for a longer period of time in order to ensure that the gas has reached the applicator and there has been enough time to enable it to fill the inside of the applicator.

A further function of microprocessor unit 40 is to activate alarms and to handle safety features and system shut down procedures in the instances when faults occur. It may be necessary to include a second microprocessor unit or a similar device into the system that can be used as a watchdog for handling safety monitoring and system shutdown procedures.

Microprocessor unit 140 may take the form of a single board computer, a microcontroller (or PIC device) a single board computer and a FIC device (used as a watch dog), more than one single board computer, more than one PIC device, a digital signal processor, or any combination of these devices.

The user interface 150 provides a means of allowing the user to control the system and provides information to the user regarding the status and operation of the system. The user interface may be in the form of a touch screen display, a flat LCD display and a set of membrane keys, or any other means of outputting and inputting user information.

The sub-system responsible for the control of the gas or gas mixture comprises of at least one gas cylinder 410 and/or a compressed air generator 420, a means of controlling the rate of flow of the gases, and a means of mixing the gases together. The rate of gas flow-may be controlled using a flow valve with a flow controller in combination with a suitable flow switch, which may be a solenoid switch. In specific embodiments of the invention the flow switches 430, 440 may not be implemented and the flow adjustment may be implemented using flow adjust controllers 450, 460. On the other hand, flow adjust controllers 450, 460 may be omitted and flow control may be implemented by mechanical adjustment of the valve connected to a gas cylinder 410 combined with electrical control of flow switch 430, 440. In the instance when a compressed air generator 420 is used, it may be possible to operate, the system using only flow switch 440. Gas mixer 400 may be required where more than one type of gas is used and it is necessary to optimise the mixture or vary the mixture during operation.

Gas mixer 400 may take the form of a pneumatic device, which works by balancing pressures from the input gas supplies to ensure that the component gases are mixed at the same pressure regardless of their individual inlet pressures and flow rates. The gases may be combined in a chamber fed by variable orifices, which are set by the mixing control. The mixers may be factory set for the gases specified. For example, if one considers a two gas system, the mix control can be calibrated directly in any proportion. This single control sets up the required mix. In a three gas mixer, where there are two proportional regulators, the proportionality may be set with two controls to set the total mix.

Where the flow is intermittent, i.e. for pulsed operation, a special control valve may be required to ensure accurate feeding of a ballast tank. Built in alarms and sensors may be added to monitor the pressure conditions in the mixer to ensure correct mixing conditions and to ensure that either of the cylinders are not empty.

The operation of the gas mixer 400, the flow switches 430, 440, the flow adjust controllers 450, 460, and the compressed air generator 420 is controlled using microprocessor 140, and adjustment of these devices may take place using a closed loop feedback system where the adjustments are based on the feedback signals from microwave detection unit 120 and/or photodiode detector circuit 910.

The water supply 501 may take the form of a tank or vessel that can hold a volume of water necessary to enable decontamination to be performed without the need to continuously top up the system with water, e.g. a 10 liter vessel may be used. It may be preferable to connect the water supply tank 501 to an external water supply to prevent the level dropping below a specified limit. It may be desirable to include a level sensor and an electronically operated valve to allow the water to enter the tank in a controllable manner. The signal from the level sensor will be input into microprocessor 140 and the control signals necessary to operate the valve will be provided by microprocessor 140 (the external water supply, the level sensor and the water control valve are not shown here). The water supply from tank 501 is fed into water pump 480, whose function is to deliver water under pressure into applicator 300, via feed pipes 480, 485. The operation of water pump is controlled using control signals provided by microprocessor 140. The first feed pipe 480 should be made from a material that is flexible and water tight and allows the supply of water to be conveyed from the system containing the microwave or RF source, the gas (or mixture of gases) and the mist generator to applicator 300. The water pressure will be such that the water can be pushed into centre conductor 320. The second feed pipe 485 should be formed from a low loss dielectric material that does not alter the microwave field set up inside applicator 300. The feed tube 485 may act as a tuning stub whereby introducing a capacitive or inductive reactance at the point of entry; if this is the case, it may be necessary to introduce a second tuning stub into the system to create a conjugate match or to cancel out the reactance introduced by second feed pipe 485 (this tuning stub is not shown in FIG. 5). A third feed pipe 475 is used to introduce the gas (or gas mixture) into the system. The third feed pipe may also introduce a further reactance, therefore the position of the third pipe may be arranged such that it provides the conjugate match necessary to cancel out the reactance introduced by second feed pipe 485.

Now considering applicator 300 in more detail, the embodiment given in FIG. 5 shows a microwave structure containing two impedance transformers made up of first centre conductor 310, second centre conductor 320 and common outer conductor 390. It is preferable for the lengths of the first and second centre conductors 310, 320 to be equal to an odd multiple of a quarter of the wavelength at the frequency of operation—full details of the operation of this microwave structure, together with a structure containing four transformers, is given below in the description that refers to FIGS. 16 and 17.

The microwave energy is fed into the structure via connector 180, which may be an N-type, an SMA type or an 7/16" type microwave connector. Second centre conductor 320 can be made hollow by virtue of the fact that the microwave current flows on the outside of the conductor due to a phenomenon known as the 'skin effect' and so only a fraction of the conductor is required for propagating the microwave energy, e.g. less than 0.1 mm may be required at 2.45 GHz operation when the conductor is made from a highly conductive material, i.e. copper, brass or silver. The fact that the skin effect enables the centre conductor to be hollow is used to enable a valve arrangement to be inserted inside conductor 320. This valve may be known as a needle valve and may take many forms; these will be known to a person skilled in the art. The valve arrangement shown in FIG. 5 consists of a spring 321 whose first end is fixed to the end wall of first centre conductor 310 and whose second end is connected to the first end of valve plunger or rod 322. It is preferable for the plunger or rod 322 to be made from a material that has a high relative permeability, i.e. of greater than 100, to allow a high enough force to be generated to move the rod or plunger 322 when magnetised. Possible materials that may be used to achieve this include: nickel, cobalt, manganese, chromium and iron, which are also known as ferro-magnetic materials. The rod or plunger 322 is surrounded by a coil of wire 730, which is preferably also contained within second conductor 322. It may also be preferable for the coil of wire 730 to be wound onto a non-metallic former that houses the plunger 322 and is inserted inside second centre conductor 320. A magnetising current is required to produce a magnetic field to align the magnetic domains within plunger 322 to produce a force to enable plunger 322 to move. The arrangement given in FIG. 5 depicts the situation whereby no magnetising current is applied to coil 730 and the valve is open and so water will flow along second centre conductor 320. A seal or washer 323 is fixed to the inner wall of second centre conductor 320 and when second end of plunger 322 is pushed against the seal 323, the water flow along the conductor can be blocked off.

The distal end of second centre conductor 320 contains a nozzle 324, which is used to atomise the water molecules that come out of the end of conductor 320 to enable a mist to be formed.

The magnetising current required to move plunger or rod 322 is provided by a current source 700. The current source 700 may be a voltage controlled current source, which may take the form of MOSFET where the level of gate-source voltage ($V_{gs}$) governs the drain current ($I_d$) flowing through the coil 730, or a current controlled current source, which may take the form of a bipolar junction transistor (BJT), where the base current ($I_r$) controls the collector current ($I_C$) that flows through the coil. Alternatively, it may be preferable to use an operational amplifier configured as a voltage controlled current source, which can be set up to allow a high impedance voltage source, or signal, available from a digital to analogue converter (DAC) contained within a microprocessor 140 to control the level of current flowing through the solenoid or coil 730.

Figure 18:
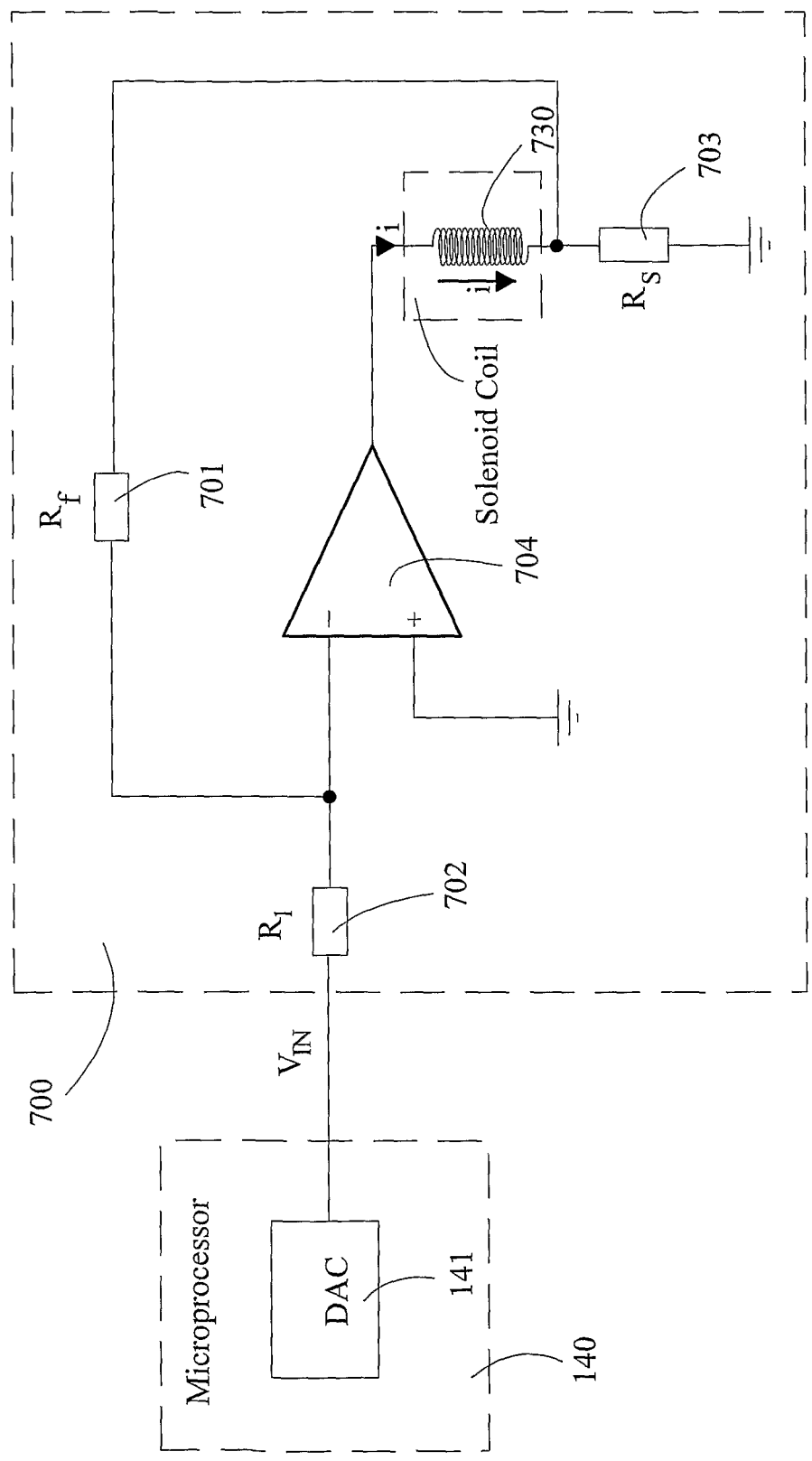
FIG. 18 is a schematic view of the control circuit for a valve to be used in an applicator according to an embodiment of the invention.

A circuit for such a voltage controlled current source is given in FIG. 18, which shows an arrangement consisting of an operational amplifier configured as a voltage-to-current converter, where the current (i) flowing through coil or solenoid 730 to produce a force (F) to move the plunger 322 can be expressed as $$i = -\left[\frac{V_{in}R_f}{R_s R_1}\right],$$

where $V_{in}$ is the voltage from DAC 141 contained within microprocessor 140, $R_f$ is the resistance of feedback resistor 701, $R_s$ is the resistance of current sense resistor 703, and $R_1$ is the resistance of input resistor 702.

A possible operational amplifier that could be used to implement this circuit is a PA05 or PA05A power operational amplifier from Apex Microtechnology Corporation; this device can deliver up to 30 A of current and a rail to rail voltage of up to 100V.

Second centre conductor 320 also contains inlet pipes for the water supply 485 and for the gas (or gas mixture) 475. These pipes are preferably made from a low loss dielectric material that does not affect the propagation of the microwave field within the structure. Alternatively, the pipes may be made from metallic sections and arranged to form two stubs that have a reactance of equal magnitude, but opposite sign at the frequency of operation in order to cancel one another out and have no net affect on the microwave field.

An array of photo diodes 900 and detector circuit 910 is also included in FIG. 5 to enable the wavelength and the intensity of the energy produced by the system to be monitored and for this information to be used in a feedback loop to control the output energy. The information gathered from the photodiodes may be used to vary the following parameters in order to optimise the spectral content or the output energy: gas mix, gas flow rate, microwave power level, modulation frequency (or format) and the quantity of mist or fog being generated. Particular devices that may be used as the detectors include silicon photodiodes, silicon PIN diodes, multi-element type silicon photodiodes and silicon avalanche photodiodes. Photodiodes are semiconductor light sensors that generate a current or voltage when the P-N junction in the semiconductor is illuminated with light. It may be preferable for a mini spectrometer arrangement to be integrated into the system to provide the function of wavelength and intensity measurement. In such arrangements, the following types of sensors may be used: CCD sensors, CMOS linear sensors and InGaAs sensors. A particular device that may be considered is a C10082MD or C10083MD mini-spectrometer from Hamamatsu, which employs a CMOS linear image sensor as the detector. These devices can be used to measure light intensity within the UV and near IR range of wavelengths. A range of sensors may be employed to enable light intensity measurements to be made within the 200 nm to 2200 nm wavelength range. It may be preferable to use a polychromator type arrangement whereby a grating is used as the wavelength dispersing element and an array type detector is placed along the focal plane of the focussing lens. Polychromators are designed to allow simultaneous detection of multiple spectra, which could be advantageous for use the invention.

Figure 6:
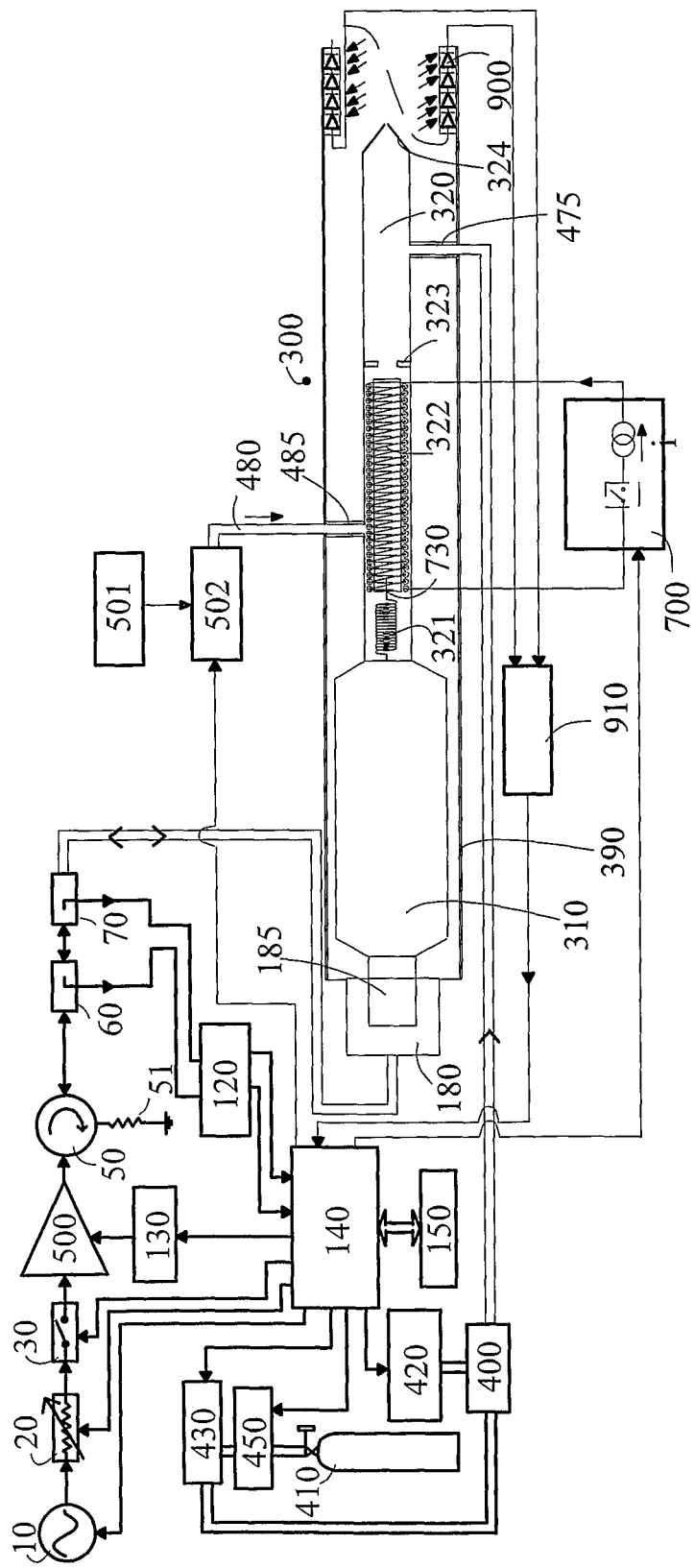
FIG. 6 is a schematic diagram of another sterilisation system for producing hydroxyl radicals without an automatic tuning mechanism.

FIG. 6 shows a similar arrangement to that shown in FIG. 5, but where the plasma is struck and maintained without the use of tuning filter 100, and stub adjuster 110. In this instance, applicator 300 may be arranged to produce a high enough electric field to enable the ionisation discharge to taken place. The mist or fog is then introduced in a similar manner to enable concentrations of OH radicals to be produced. In this arrangement, it may be preferable for the microwave energy to be delivered as a train of pulses, where each pulse produces a plasma strike, to enable a quasi continuous plume of plasma to be generated, e.g. the microwave energy delivery profile may consist of a continuous train of pulses that are ON for a time period of 1 ms and OFF for a time period of 10 ms. The pulse repetition rate and the pulse length may be used to determine the plasma energy and this may be optimised to enable the desired concentration of OH radicals to be produced at the end of the applicator. Due to the need to only monitor the forward and reflected power between the output of power circulator 50 and the input to microwave cable assembly 200, only two couplers 60, 70 are required to implement this embodiment of the invention. It may be preferable for reflected power coupler 70 to be connected between the third port of protection circulator 50 and the non grounded end of dump load 51 in order to provide increased measurement signal directivity, which will lead to more accurate measurement information available to microprocessor 140.

Figure 7C:
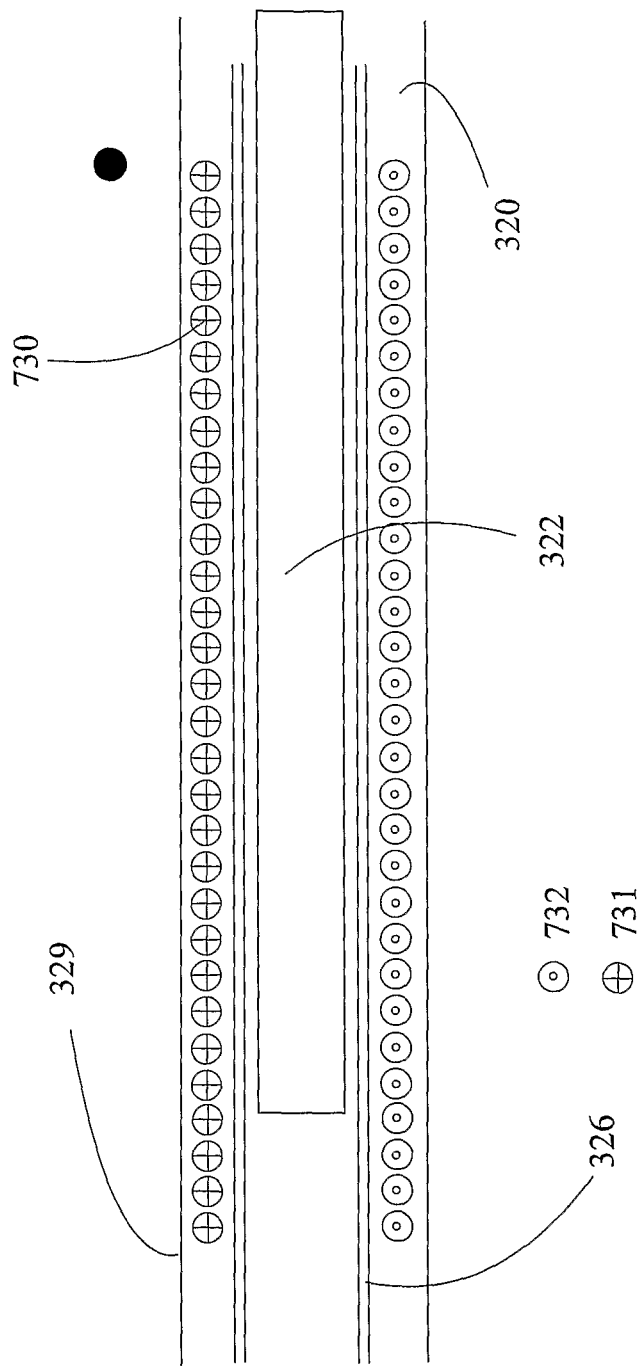

FIGS. 7(*a*), 7(*b*) and 7(*c*) show the needle valve arrangement in more detail. FIG. 7(*a*) shows the state of the plunger 322 without the magnetising force being applied. It can be seen that the magnetic domains 328 are in disorder or in a random state. FIG. 7(*a*) shows the valve in the closed position, where the end of the plunger 322 is pushed up against the seal 323. Spring 321 is shown in the extended state. The spring 321 may be a rigid spring if the device is to be usefully set up in this arrangement since the extended spring must ensure that plunger 322 is held tightly against seal 323 to prevent any leakage of water. It may be preferable to change this configuration to extend spring 321 when a magnetising field is set up to move the plunger 322 to a position where the valve is closed and when the field is removed, the spring tension is also removed to enable plunger 322 to be released to open the valve. In the arrangement shown here, a solenoidal winding is wound around a former 326, which is preferably made from a non-magnetic material, e.g. a plastic or nylon. The former 926 is inserted inside centre conductor 320. The coil winding 730 preferably uses an enameled coated wire to allow adjacent turns to touch one another without producing a single shorted turn; this also allows multi layer windings to be used which, in turn, increase the magnitude of the force that can be set up to move the plunger. In the arrangements illustrated here the 'dot' above the winding indicates the start of the winding, 'x' 731 indicates that the wire is going into the page and the '•' 732 indicates that the wire coming is coming out of the page. FIG. 7(*b*) shows the situation where the current source 720 is switched ON (illustrated here by a switch closure initiated by a signal from microprocessor 140), which sets up a magnetising force to enable all of the magnetic domains 328 to become aligned in one particular orientation, which generates a force F, which, in turn, causes plunger 322 to move, whereby spring 321 becomes compressed. The movement of plunger 322 also enables the water tight seal, formed by the end of plunger 322 pushing against washer or seal 323, to be broken. The force F that is set up is determined by the relative permittivity of plunger 322, the number of turns of wire 730 around former 326 and the level of current i available from current source 720. The relationship between these parameters is best described by equation 5 given below:

$$F = \mu_0 \mu_r N i^2,$$

where $\mu_0$ is the permeability of free space ($4\pi \times 10^{-7}$ H/m), $\mu_r$ is the relative permeability (or flux multiplier) of magnetic material, N is the number of turns wrapped around the former.

For example, if the coil is wound with 150 turns, the plunger is made from a material with a relative permeability of 150, and a pulsed current of 10 A is applied to the coil, the force available will be 4.71 N.

Figure 8:
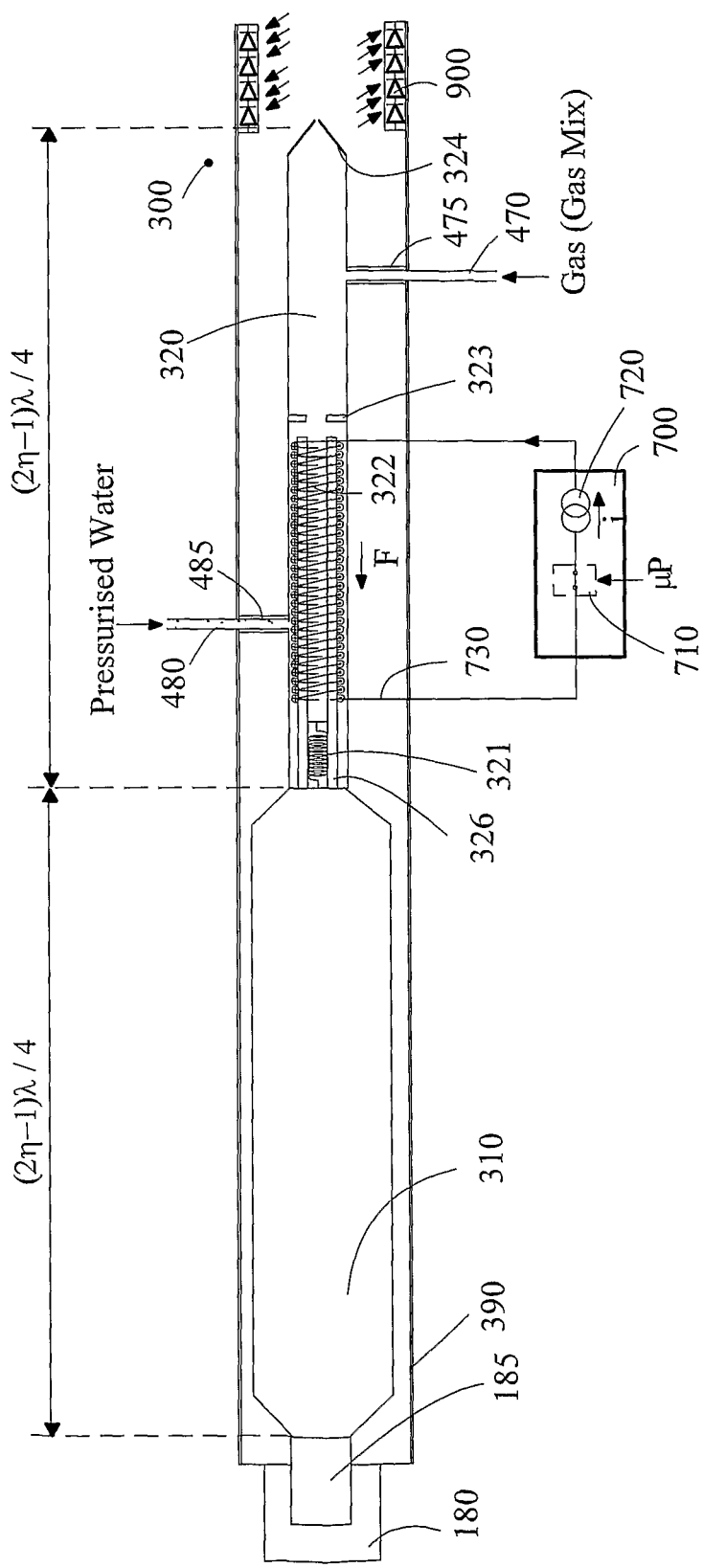
FIG. 8 is a longitudinal cross-sectional view of a coaxial plasma applicator having two impedance transformers and an inbuilt valve in an open configuration.

FIG. 8 shows an embodiment of a complete applicator in accordance with the current invention, where a two quarter wave transformer sections 390-310 and 390-320 are used and the valve used to control the water supply to create the mist is contained inside the second transformer as described above. In the arrangement shown in FIG. 8, voltage controlled switch 710 is closed and current source 720 is turned ON, which energises coil 730, which sets up a force (F) to move plunger 322, which causes the valve to open to allow a mist to be generated at nozzle 324 at the end of centre conductor 320.

Figure 9:
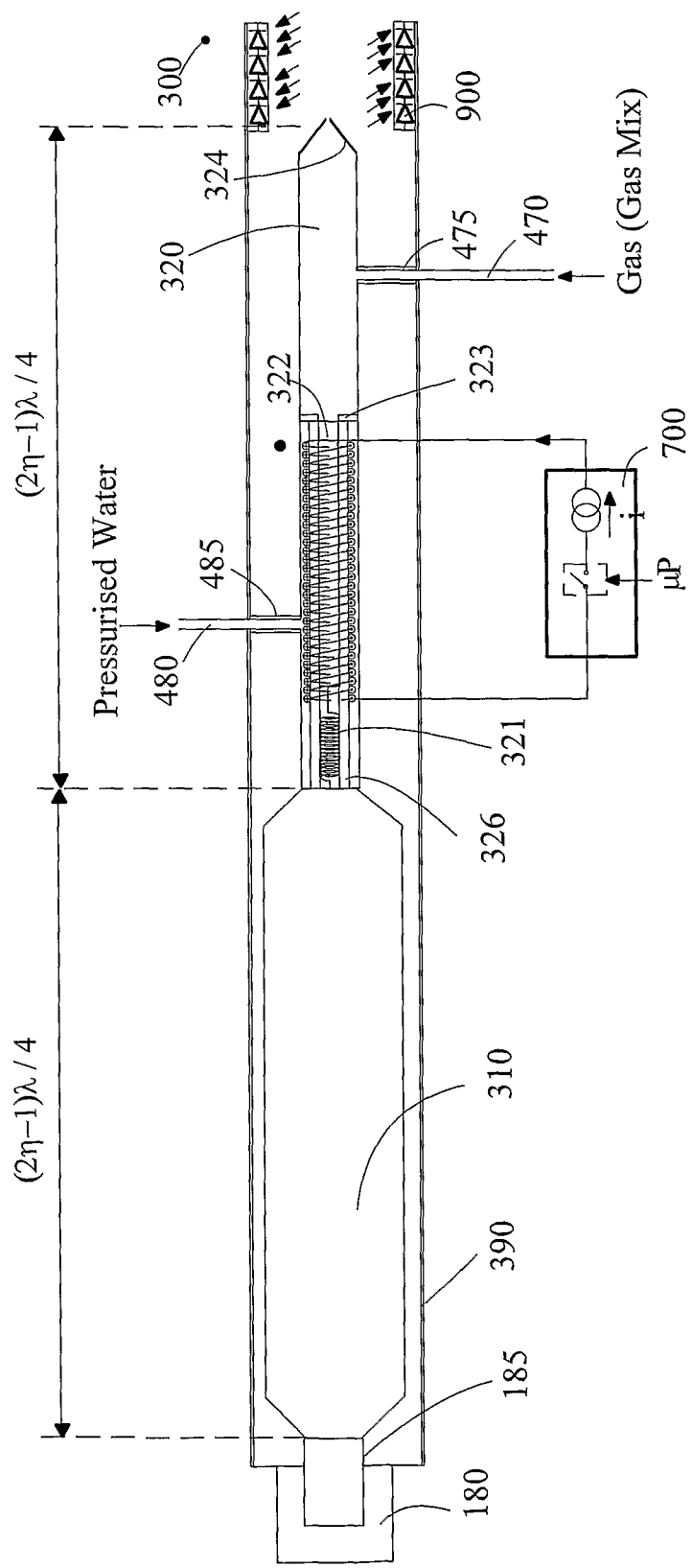
FIG. 9 is a longitudinal cross-sectional view of the coaxial plasma applicator shown in FIG. 8 in a closed configuration.

FIG. 9 shows a similar arrangement whereby current source 720 is switched OFF, which closes the valve, which prevents the mist from being formed at the end of centre conductor 320.

Figure 10:
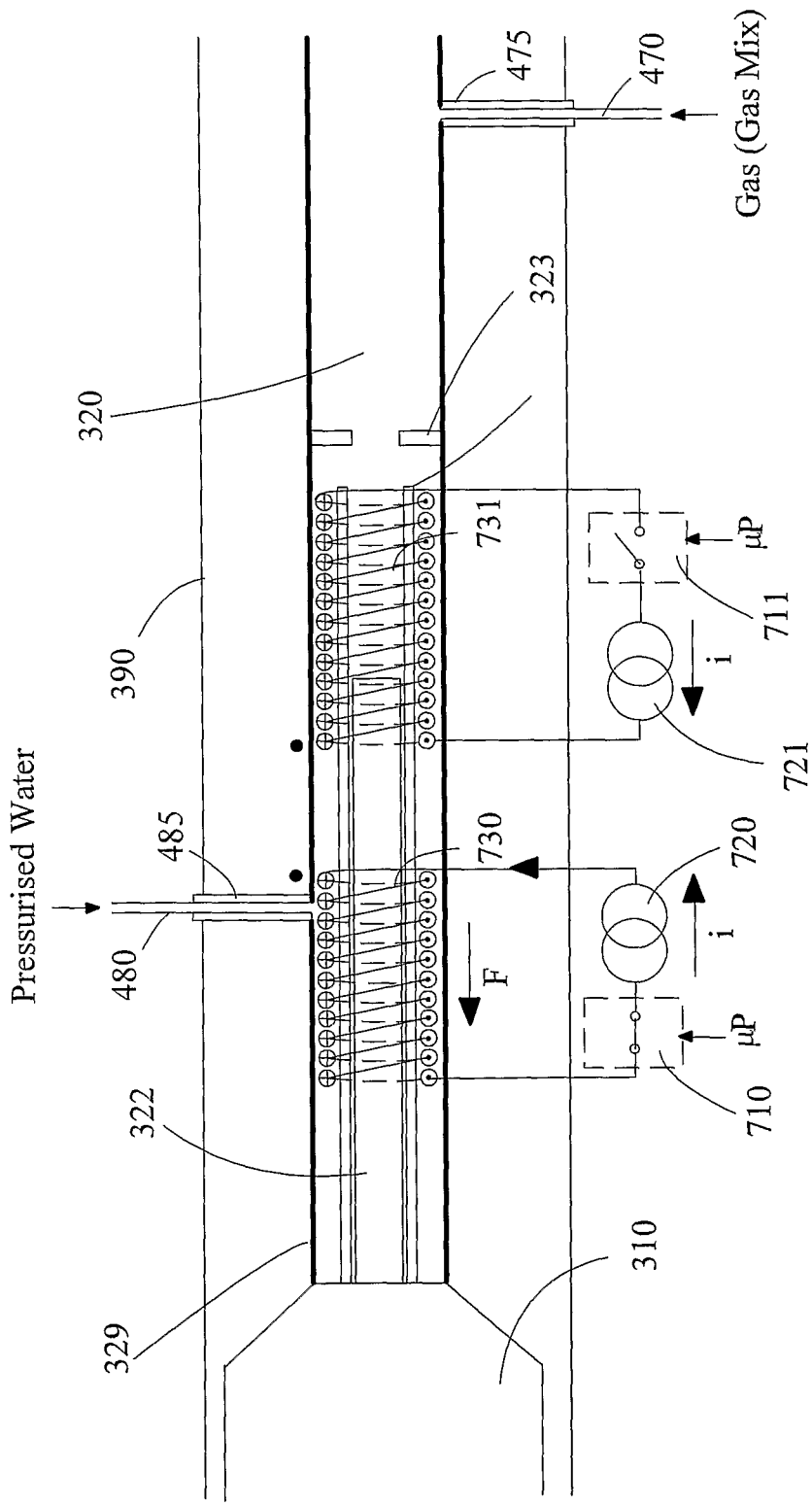
FIG. 10 is a partial longitudinal cross-sectional view of a coaxial plasma applicator having an inbuilt valve operated using two windings in an open configuration.
Figure 11:
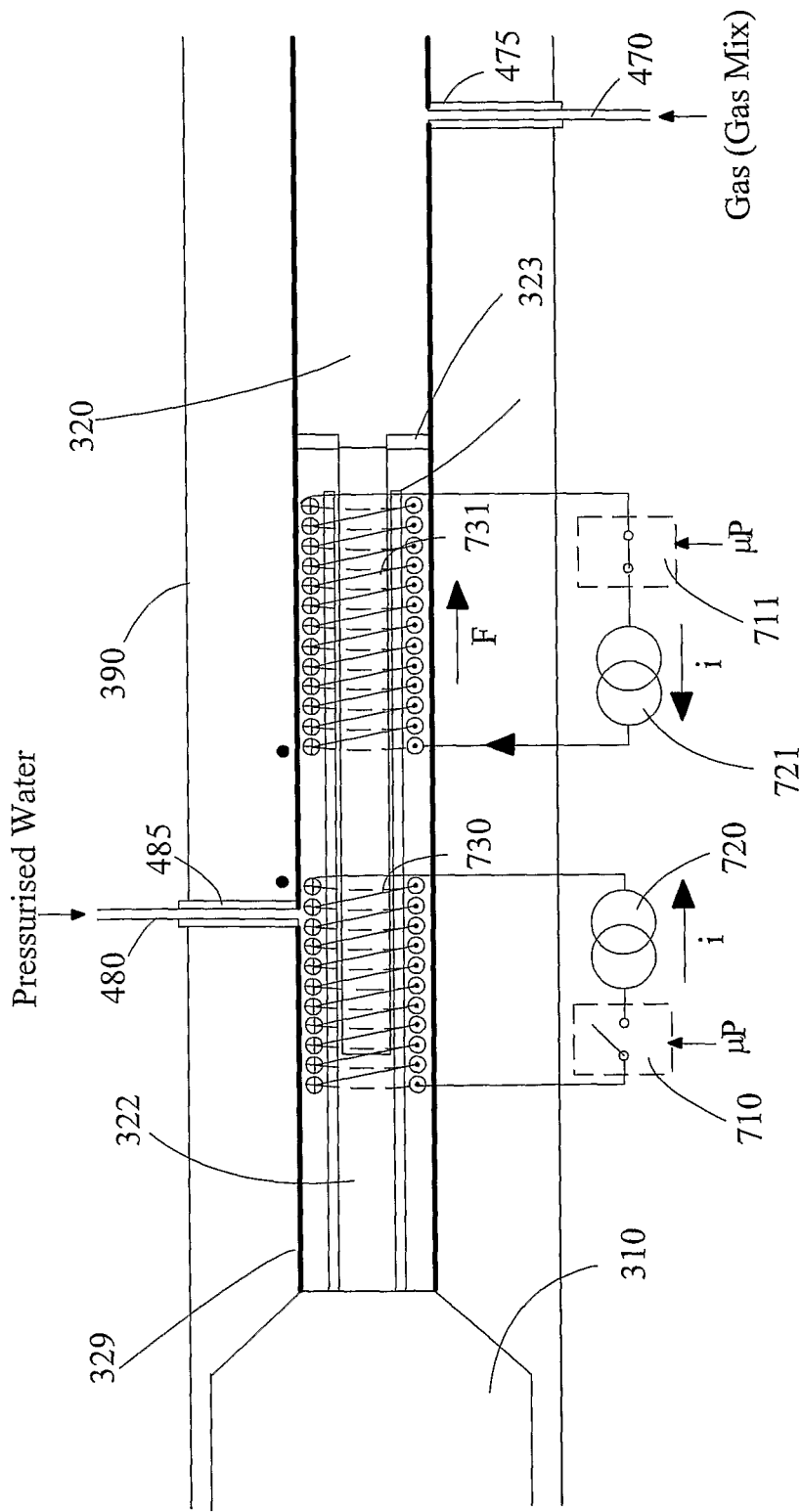
FIG. 11 is a partial longitudinal cross-sectional view of the coaxial plasma applicator shown in FIG. 10 in a closed configuration.

FIGS. 10 and 11 shows an alternative arrangement where two solenoids or windings 730 and 731 are independently excited in accordance with signals produced by microprocessor 140 to enable plunger 322 to be moved to enable the valve to be opened and closed. In the arrangement given in FIG. 10, first current source 720 is turned ON, which sets up a magnetising force in winding 730 to create a physical force (F) in a direction that moves the plunger 322 towards first conductor 310, which opens the valve to enable the pressurised water to flow along centre conductor 320. In the arrangement given in FIG. 11, second current source 721 is turned ON, which sets up a magnetising force in winding 731 to create a physical force (F) in a direction that moves the plunger 322 towards the seal 323, which closes the valve to prevent water from flowing along the of centre conductor 320. It should be noted that current sources 720 and 721 are set up to drive the current through their respective windings 730 and 731 in opposite directions in order to align the magnetic domains in opposite directions, i.e. the direction of the magnetic domains are reversed, to enable the plunger 322 to be moved in a direction that is in accordance with the winding currently activated.

Figure 12:
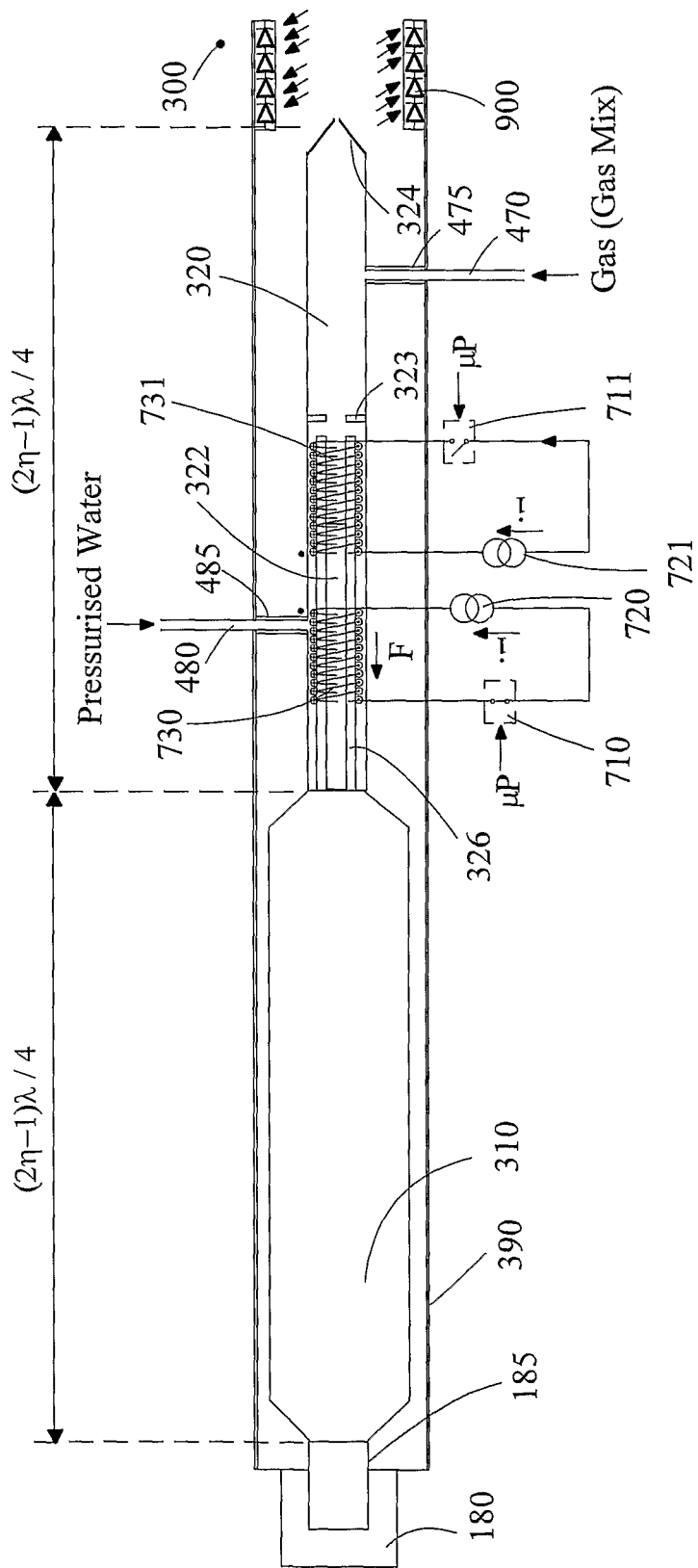
FIG. 12 is a full longitudinal cross-sectional view of the coaxial plasma applicator shown in FIG. 10.
Figure 13:
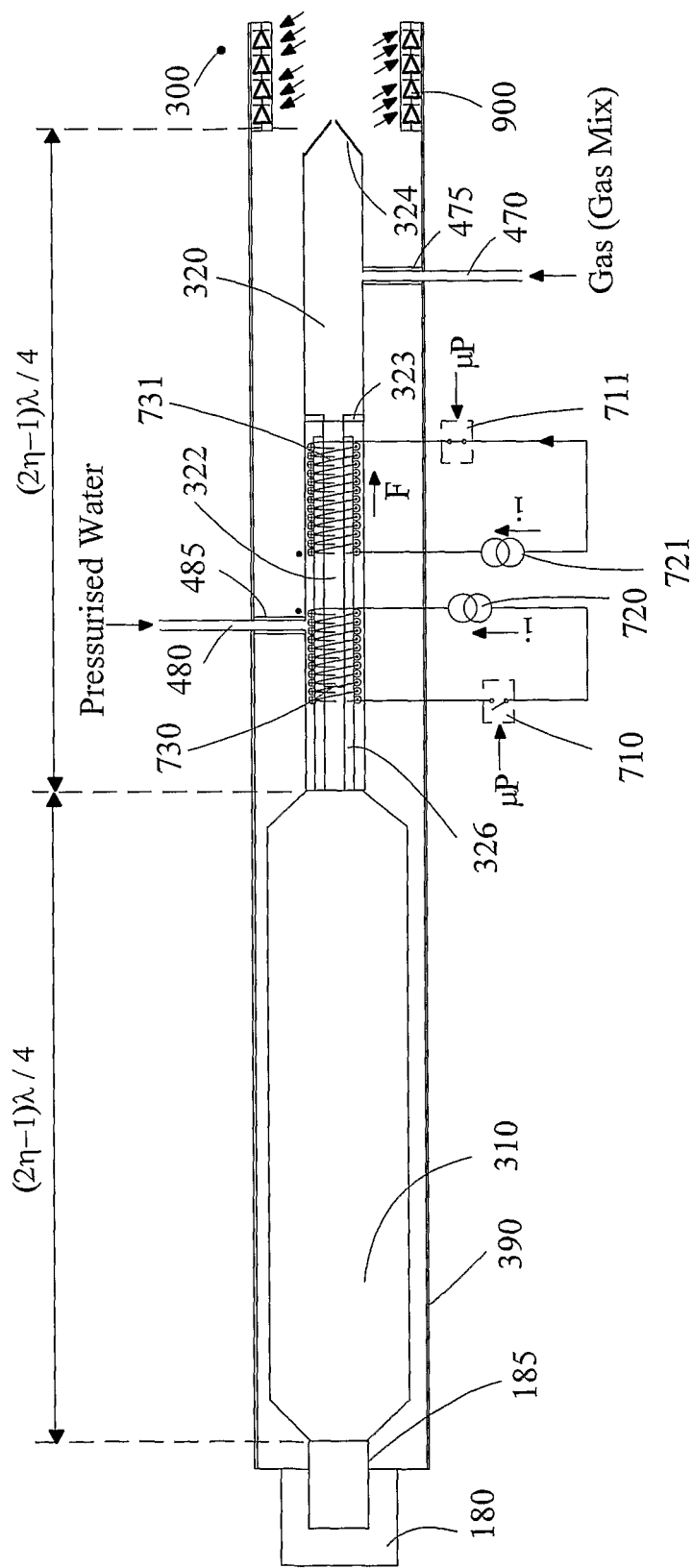
FIG. 13 is a partial longitudinal cross-sectional view of the coaxial plasma applicator shown in FIG. 11.

FIGS. 12 and 13 show an embodiment of a complete applicator in accordance with the current invention, where a two quarter wave transformer sections 390-310 and 390-320 are used and the valve used to control the water supply to create the mist is contained inside the second transformer 320 as described above. In the arrangement shown in FIG. 12, when voltage controlled switch 710 is closed, current source 720 is turned ON and coil 730 is energised; this sets up a force 'F' which moves plunger 322 to a position whereby its first end is held against the second end of first conductor 310; the valve is in the open position and pressurised water from feed pipes 480 and 485 is able to flow along or through centre conductor 320, where the water molecules are atomised at the end by nozzle 324 to create a suitable mist. Gas (or a gas mixture) is also fed into centre conductor 320, via feed pipes 470 and 475, and used to assist in pushing the water out of the end of centre conductor 320 and also assist in the plasma generation process. In the arrangement shown in FIG. 13, voltage controlled switch 711 is closed and current source 721 is turned ON, which causes coil 731 to be energised. This sets up a force 'F' which moves plunger 322 to a position whereby its second end is pushed against seal 323 and so the valve is in the closed position, which prevents the flow of pressurised water, from feed pipes 480 and 485, along or through centre conductor 320. Gas (or a gas mixture) is still fed into centre conductor 320, via feed pipes 470 and 475, to enable the plasma generation process to take place and so sterilisation plasma is produced at the end of applicator 300.

Figure 14:
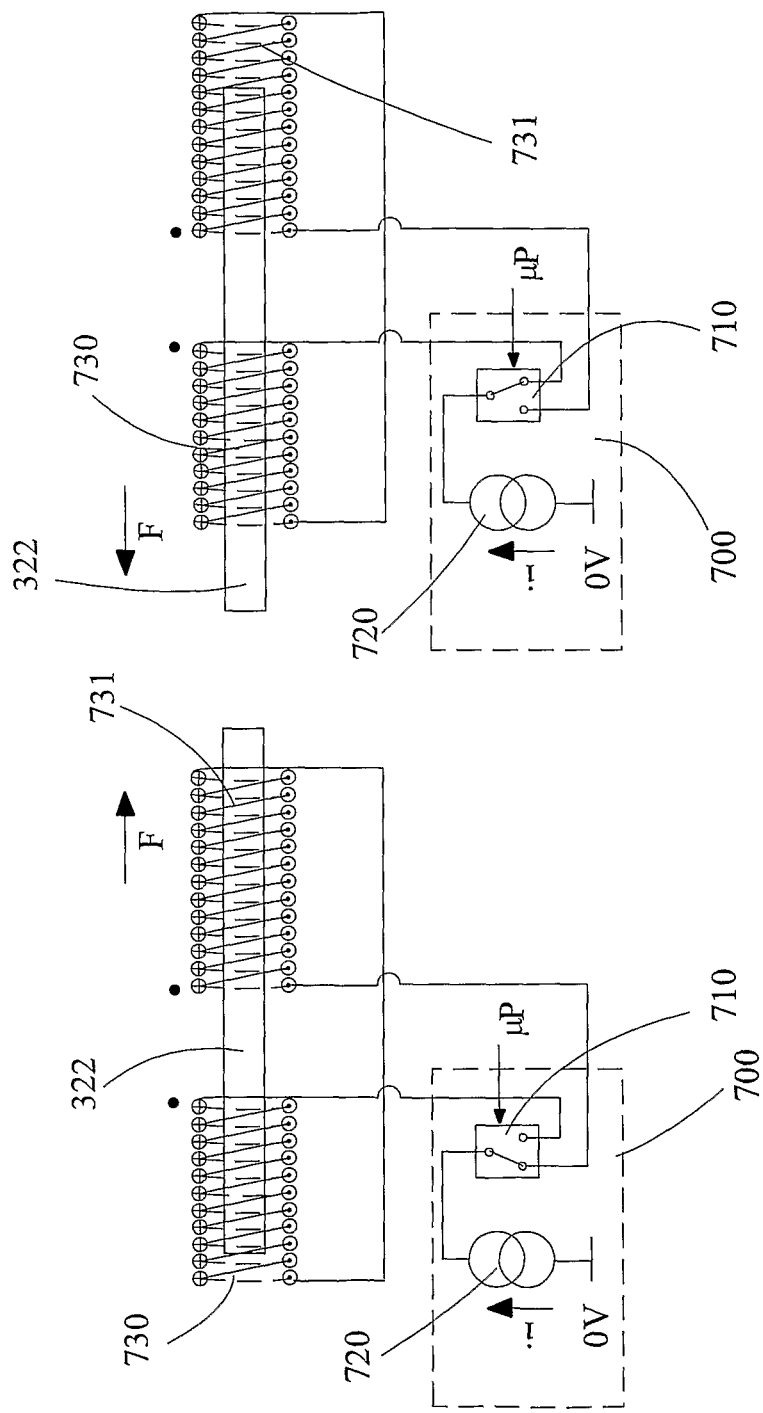
FIGS. 14(*a*) and 14(*b*) are schematic views of the control circuit for a valve to be used in an applicator according to an embodiment of the invention.

FIGS. 14(*a*) and 14(*b*) give arrangements whereby a single current source 720 and an electronically controlled single-pole-double-throw switch is used to energise either the first or second coil in accordance with the switch contact position. FIG. 14(*a*) shows the arrangement whereby the first coil is energised and the second coil is de-energised to enable the valve 322 to be moved towards the right of the page (corresponding to a valve closure and no mist being generated). FIG. 14(*b*) shows the arrangement whereby the second coil is energised and the first coil is de-energised to enable the valve 322 to be moved towards the left of the page (corresponding to the valve being opened and a mist being generated). The direction of the current flow within the windings is set up to enable the force produced by the current to move the valve or plunger 322 in opposite directions when the position of switch 710 is changed.

Figure 15:
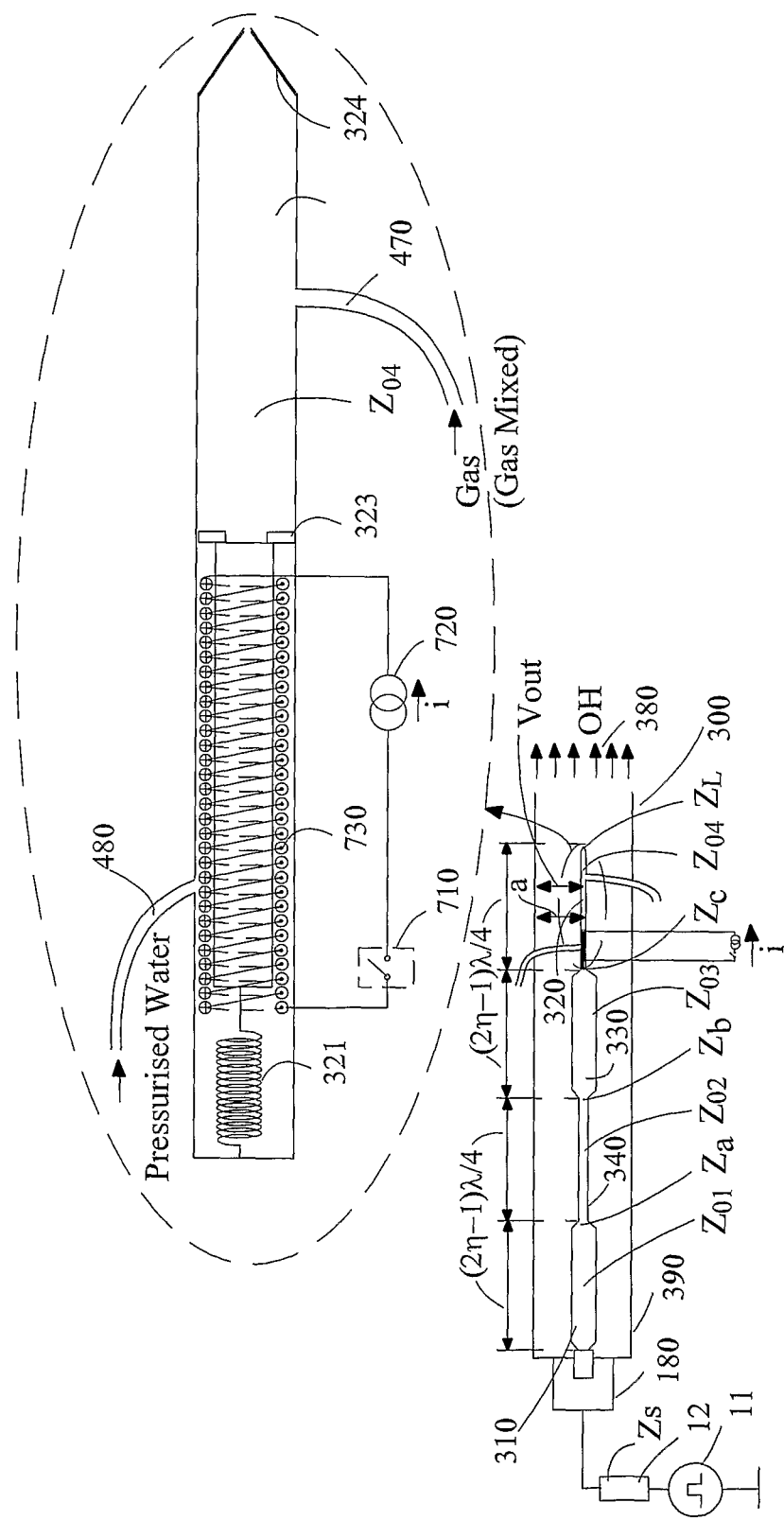
FIG. 15 is a longitudinal cross-sectional view of a coaxial plasma applicator having four impedance transformers and an inbuilt valve in an closed configuration.

FIG. 15 shows a valve arrangement similar to that described with reference to FIGS. 8 and 9, but where the structure contains four quarter wave impedance transformers to generate the electric field required to cause the ionisation discharge necessary to produce plasma and OH radicals. This transformer arrangement is described in more detail below with reference to FIG. 17, where the significance of the low impedance quarter wave sections 310, 330 ($Z_{01}$, $Z_{03}$) and the high impedance quarter wave sections 320, 340 ($Z_{02}$, $Z_{04}$) and the physical arrangement of these transformer sections is addressed in detail.

Figure 16:
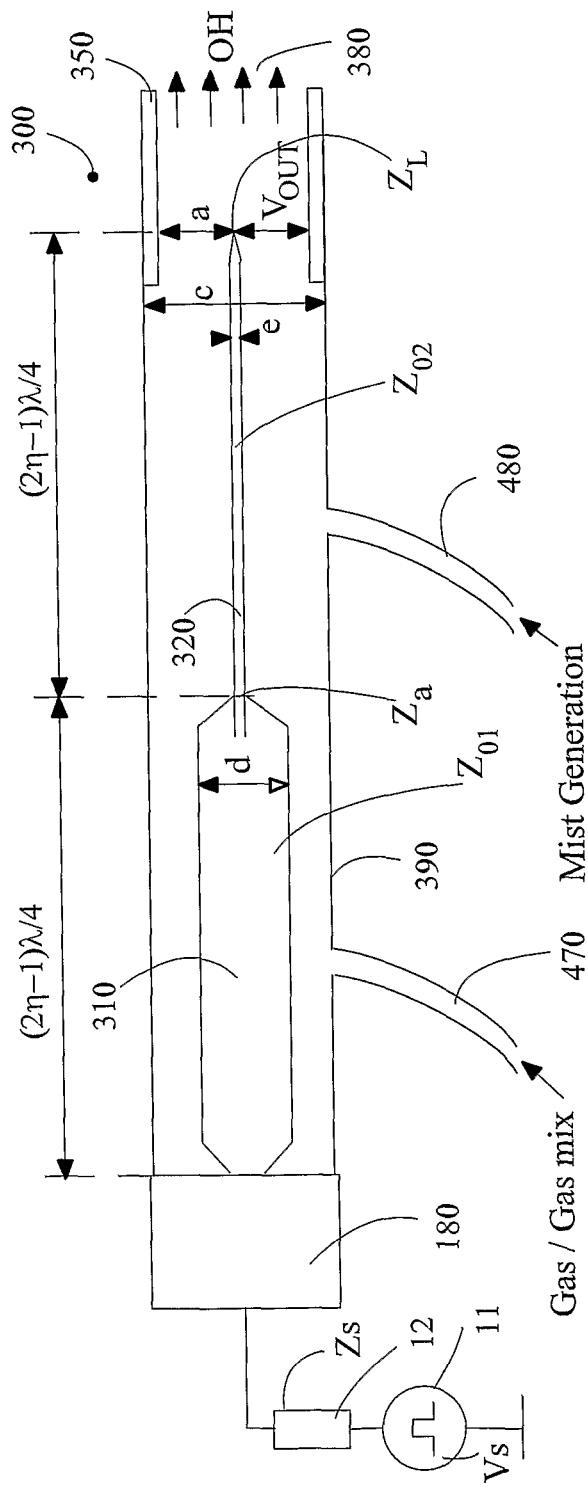
FIG. 16 is a longitudinal cross-sectional view of a coaxial plasma applicator having two impedance transformers in which gas and mist are fed through inlet in the outer conductor of a coaxial assembly.

FIG. 16 shows an applicator that uses two transformer sections 390-310, 390-320 to create the plasma with a gas (or a gas mixture) fed into the structure using feed pipe 470 positioned near the end that contains the input connector 180 that feeds microwave energy into the structure and where the mist or fog is fed into the structure via feed pipe 480. In this structure, the first section 390-310 is a low impedance section and the second section 390-320 is a high impedance section. The length of the first and second sections is preferably equal to an odd multiple of a quarter of the wavelength at the frequency of interest. The distal end of the centre conductor in the second section 320 is pointed in order to maximise the breakdown, and the proximal and distal ends of the centre conductor in the first section 310 are tapered to ensure that the transition from the 50Ω generator to a lower impedance introduced by the first transformer and from this impedance to the higher impedance of the second section are as gradual as possible. In a particular embodiment, an angle of 45° may be chosen. The lengths of the first and second sections 310, 390 are preferably chosen to be one quarter of the wavelength at the frequency of operation. In this arrangement, the impedance of the first transformer section $Z_{01}$ may be expressed as $$Z_{01} = 138 \log_{10} \frac{c}{d},$$

where c is the diameter of the inner surface on the outer conductor 390, and d is the diameter of the outer surface of the inner conductor 310. Similarly the impedance of the second transformer $Z_{02}$ can be expressed as $$Z_{02} = 138 \log_{10} \frac{c}{e},$$

where e is the diameter of the outer surface of the inner conductor 320.

The input (or generator) impedance $Z_S$ is nominally 50Ω. The load impedance $Z_L$ seen at the distal end of applicator 300 may be calculated using $$Z_L = \frac{Z_{02}^2 Z_S}{Z_{01}^2}.$$

This equation assumes that be noted that the physical length of each of the transmission line sections (transformer impedance transformers) is equal to an odd multiple of the quarter wavelength at the frequency of operation.

In a first practical embodiment of the current invention, conductors with the following dimensions were used: c=12.74 mm; d=6.34 mm, e=1 mm. Using the equations above, $Z_{01}$=41.82Ω, $Z_{02}$=152.5Ω, and $Z_L$=664.8Ω.

The input power ($P_{in}$) available from the generator, will produce a load voltage ($V_L$) equal to $V_L = \sqrt{P_{in} Z_L}$ at the distal end of applicator 300. If 1 kW of microwave power is available from the power generator, $V_L$=815.35 V. This enables an electric field of 127998 Vm$^{-1}$ to be available to strike the plasma.

In a second practical embodiment, conductors with the following dimensions were used: c=12.74 mm; d=9.5 mm, e=1 mm. In this embodiment $Z_{01}$=17.5Ω, $Z_{02}$=152.5Ω, $Z_L$=3796.94Ω, $V_L$=1948.57 V, to enable an electric field of 305898 Vm$^{-1}$ A quartz tube or quartz slices 350 are shown at the end of applicator 300, and are included for the purpose of intensifying or modifying the electric field. It is preferable to use a low loss quartz material. It has also been shown that the plasma may be struck and maintained without the use of a quartz tube.

Figure 17:
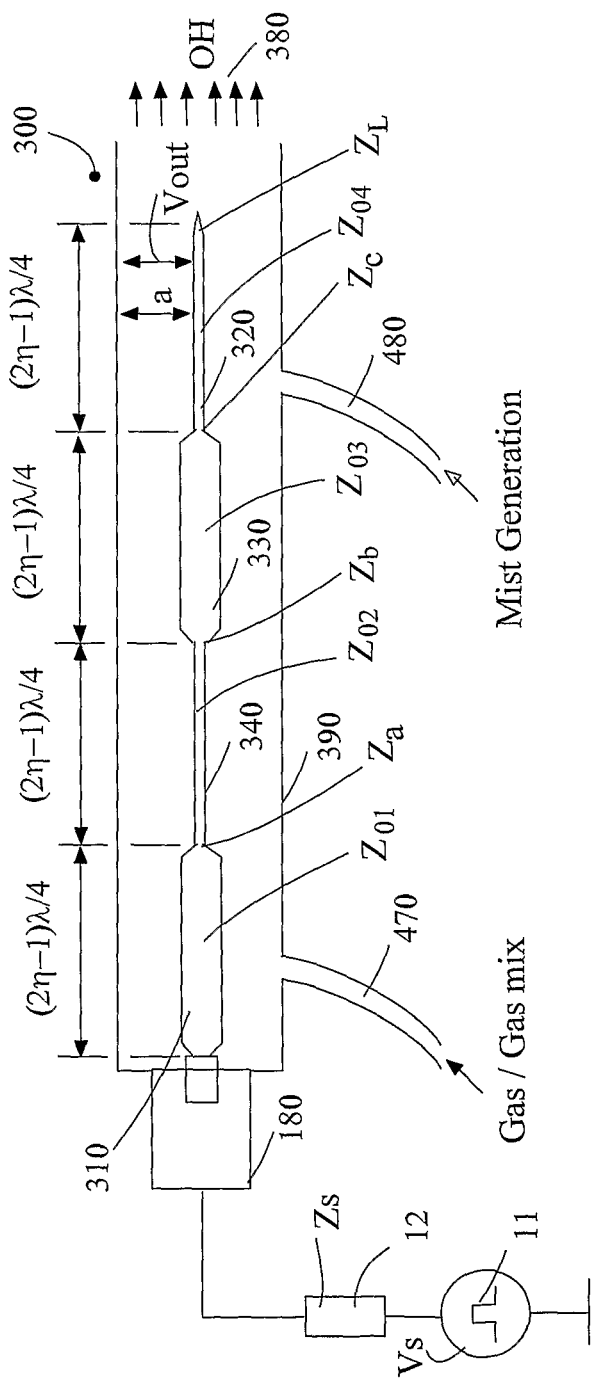
FIG. 17 is a longitudinal cross-sectional view of a coaxial plasma applicator having four impedance transformers in which gas and mist are fed through inlet in the outer conductor of a coaxial assembly.

FIG. 17 shows a similar arrangement for an applicator that may be used to create OH radicals, but where four quarter wave impedance transformer sections are used. In this arrangement, the load impedance $Z_L$ seen at the distal end of applicator 300 may be expressed as $$Z_L = \frac{Z_{04}^2 Z_{02}^2 Z_S}{Z_{03}^2 Z_{01}^2},$$

where $Z_S$ is the input (or generator) impedance, $Z_{01}$ is the characteristic impedance of the first quarter wave transformer, $Z_{02}$ is the characteristic impedance of the second quarter wave transformer, $Z_{03}$ is the characteristic impedance of the third quarter wave transformer, and $Z_{04}$ is the characteristic impedance of the fourth quarter wave transformer.

Assuming that the applicator structure is lossless, i.e. ignoring power loss along the length of the structure, hence power in=power out, the electric field E set up at the distal end of fourth section 390-320, which is used to create the ionisation discharge may be expressed as $$E = \frac{\sqrt{P_{out} Z_L}}{a},$$

where $P_{out}$ is the output power and a is the distance between the tip of centre conductor contained within the fourth transformer and the inner wall of the outer conductor of the applicator.

A practical embodiment may have $Z_{01}$=$Z_{03}$=10Ω, $Z_{02}$=$Z_{04}$=100Ω, $P_{in}$=$P_{out}$=1000 W, and a=10 mm. Accordingly, in this embodiment, $Z_L$=500 kΩ and $V_L$=22.4 kV, which enables an electric field of 2.23 MVm$^{-1}$.

It can be seen from this analysis that this arrangement may be used to create extremely large electric fields to enable suitable ionisation discharges to be created in small applicator structures to enable high concentrations of OH radicals to be produced for effective decontamination or sterilisation to be performed.

Figure 19:
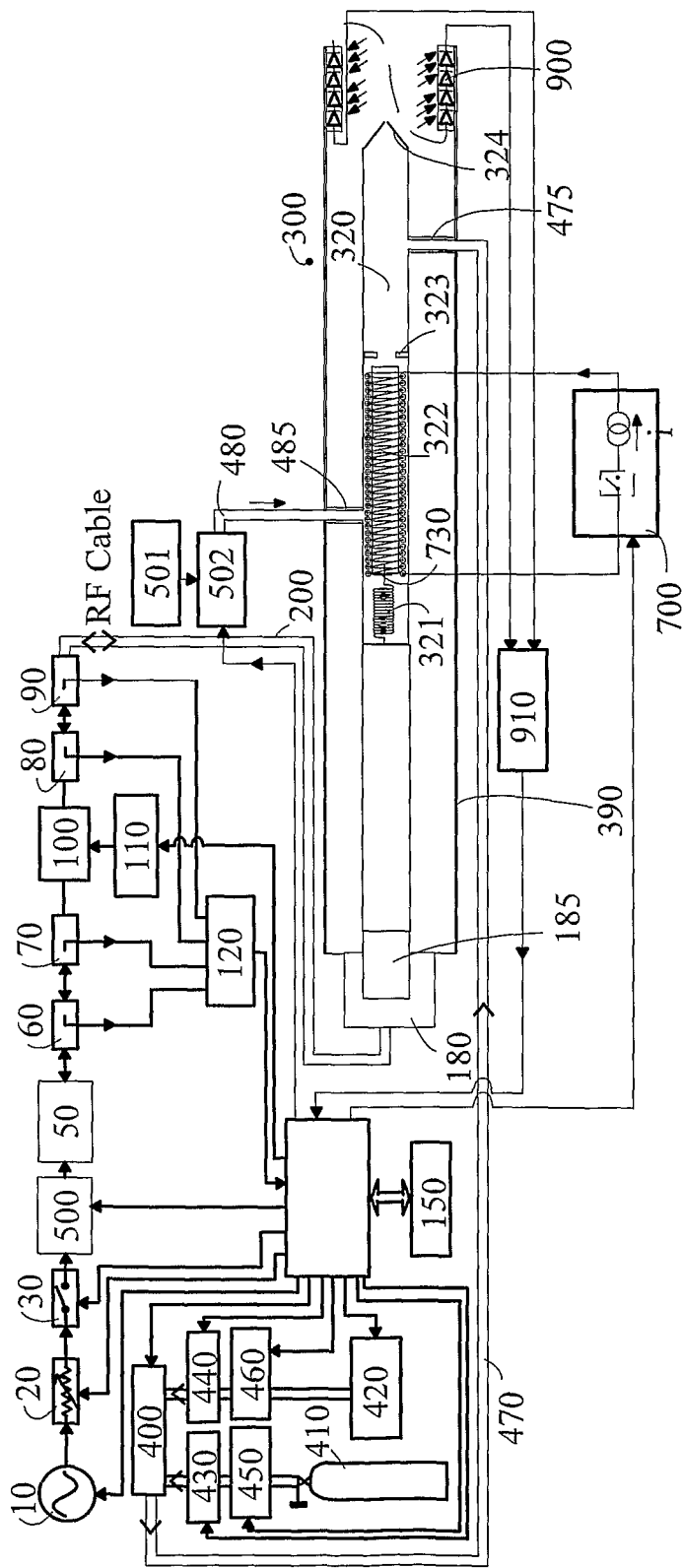
FIG. 19 is a schematic diagram of a sterilisation system for producing hydroxyl radicals in which the energy source is an RF generator and the applicator consists of a coaxial structure with a single centre conductor.

FIG. 19 gives a complete sterilisation system similar to that shown in FIGS. 5 and 6, but where the energy source 10, 20, 30, 500 is an RF generator rather than a microwave generator and the applicator consists of a single conductor coaxial structure made up of a single centre conductor 320 that runs from connector 180/185 to nozzle 324 and outer conductor 390. The RF amplifier 500 may be implemented using power Metal Oxide Semiconductor Field Effect Transistor (MOSFET) devices, power Bipolar Junction Transistor (BJT) devices, Insulated Gate Bipolar Junction Transistor (IGBJT) devices or the like. It may be impractical to use quarter wave impedance transformers within the structure when using lower RF frequency energy sources. In this configuration, the matching circuit 100 would be made up of lumped element inductors and capacitors and the variation in capacitance and inductance could be implemented using an arrangement of motor driven actuators, e.g. a linear motor may be connected to a single (or a stack) of moveable plates in order to move it/them in and out of a fixed plate (set of plates) to vary the value of tuning capacitance. A further linear actuator may be connected to a moveable wiper that makes contact with a fixed inductive winding to enable the value of inductance to be varied. The matching circuit may take the form of a two lumped element L-network or a three lumped element π- or I-network.

Figure 20:
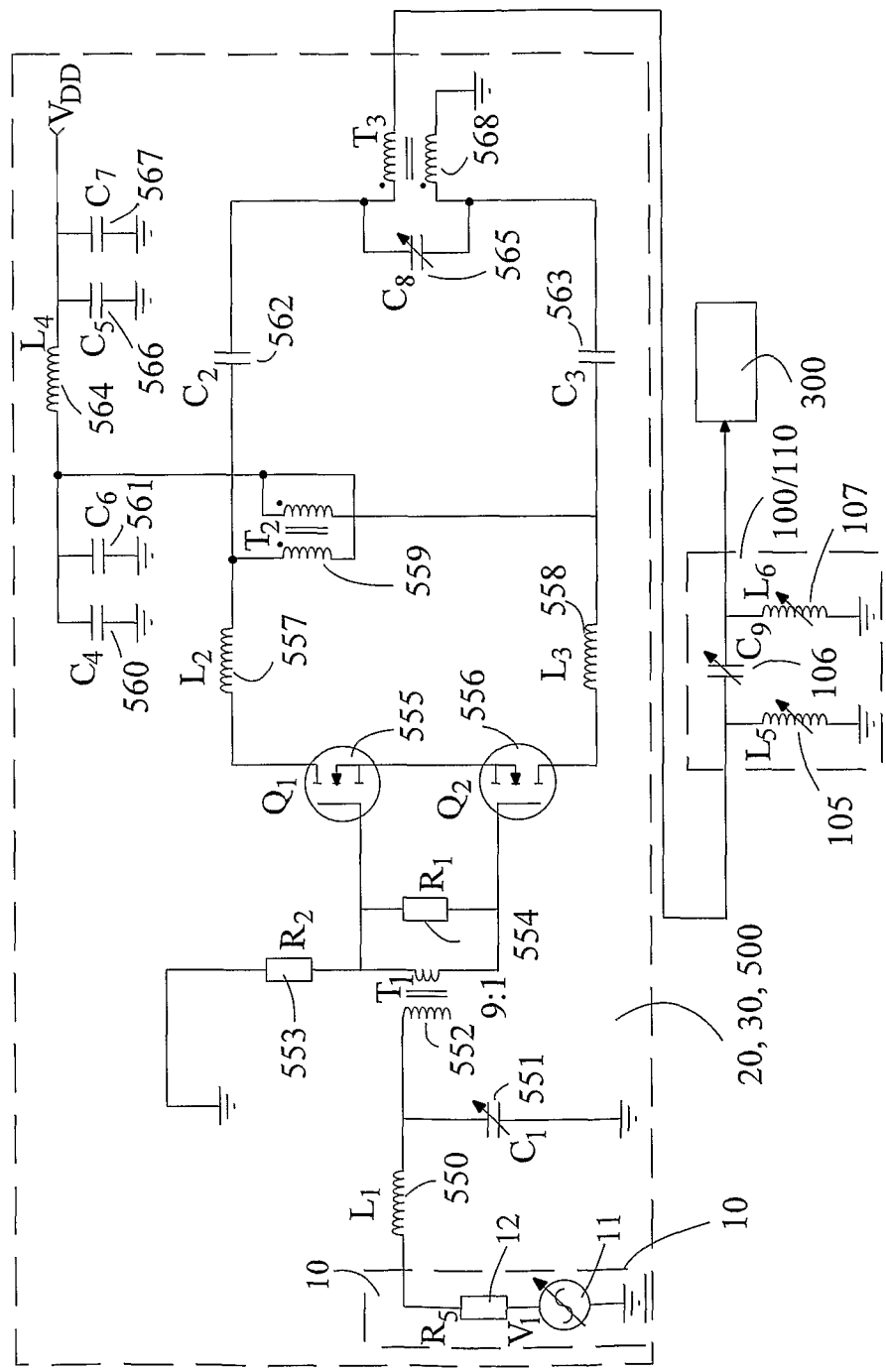
FIG. 20 shows an embodiment of an RF generator suitable for use in the system shown in FIG. 19.

FIG. 20 gives a circuit for an RF generator 20, 30, 500 that uses two power MOSFETs connected in a push-pull configuration and a π matching filter 100 is used to match the impedance at the output of the RF generator with the impedance set up inside applicator structure 300. In the particular arrangement shown here, it is desirable for the amplifier to be designed around a symmetric pair of common source RF power MOSFETs $Q_1$ and $Q_2$ 555, 556 housed in a TO-247 package. Particular devices that may be used to implement the design are ARF448A and ARF448B symmetric pair from Advanced Power Technology (APT). These particular devices are targeted at high voltage single frequency class C operation primarily in the 13.56 MHz, 27.12 MHZ and 40.68 MHz ISM bands. At 50 MHz these devices provide a power gain of about 17 dB. The input gate matching circuit shown in the diagram uses a transformer $T_1$ 552 and L-tuned network comprising inductor $L_1$ 550 and capacitor $O_1$ 551. The transformer $T_1$ 552 provides the balanced feed required by the push-pull arrangement $Q_1$ and $Q_2$ 555, 556 as well as a 9:1 transformation. At the output, variable capacitor $C_8$ 565 forms a part of a further L-network. A choke 559 is a shunt feed bifilar choke, which is on the low impedance end of compensating chokes $L_2$ and $L_3$ 557, 558 to ensure that the RF voltage across it is small to prevent the toroidal core used in choke $T_2$ 559 from saturating due to too much voltage being applied across it. The output coupling capacitors $C_2$ and $C_3$ 562, 563 have a large surface area to enable them to carry high levels of RF current. A transformer $T_3$ 568 is arranged as a 1:1 coaxial balun. The lumped element impedance matching circuit is a π arrangement comprising of two shunt inductors $L_s$ and $L_6$ 105, 107 and series capacitance $C_9$ 106. These three tuning elements can be adjusted to enable the high impedance plasma strike and the low impedance plasma maintain conditions to be set up with applicator 300. The impedance matching may be performed automatically using linear or stepper motors, linear actuators (solenoid or magnetostrictive types), moving coil arrangements or the like. The tuning adjustments may be made based on voltage and current information measured at the input and output ends of tuning network using voltage dividing networks, e.g. reactive dividers made up of two capacitors in series, and current transformers respectively. The output from the π matching circuit 100 is connected to the applicator 300 via a suitable cable assembly (not shown here). The applicator 300 may take a similar form to the arrangement shown in FIG. 19.

Figures 21A, 21B:
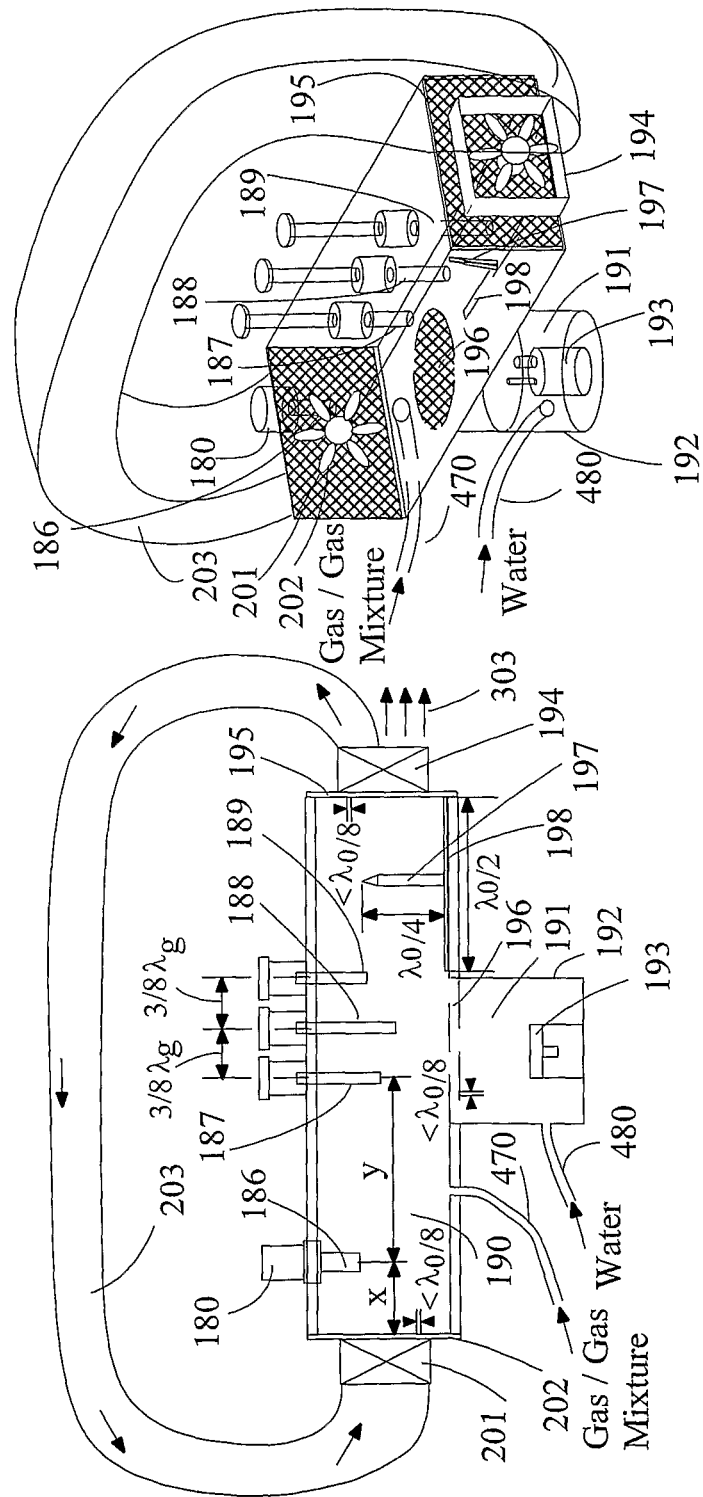
FIGS. 21(*a*) and 21(*b*) are views of a first plasma applicator according to an embodiment of the invention.

FIGS. 21(a) and 21(b) show a device that may be used to generate concentrations of OH radicals suitable for decontaminating an enclosed space whereby a number of bacteria, spores, and viruses may be destroyed. This system may also be used to destroy prions. The arrangement consists of a waveguide cavity 190, which may be a standard waveguide design, e.g. WG6 (1.12 GHz to 1.7 GHz), WG7 (1.45 GHz to 2.2 GHz), WG8 (1.7 GHz to 2.6 GHz), WG9A (2.2 GHz to 3.3 GHz), WG10 (2.6 GHz to 3.95 GHz) or WG11A (3.3 GHz to 4.9 GHz), the cavity of a microwave oven or a hollow rectangular or cylindrical section whose dimensions allow microwave energy at the frequency of operation to propagate with low loss. It may be preferable to design the cavity such that the dominant $TE_{10}$ mode propagates in the rectangular guide or the dominant $TE_{11}$ mode propagates in the circular or cylindrical guide. The internal dimensions of the waveguide cavity determine the range of frequencies that can propagate within the cavity and place a limitation on the size of components or elements, e.g. tuning elements, stubs, rods, electrodes or antennas used to assist the generation of the high energy ionisation discharges.

The waveguide cavities that were considered here for embodiments of the current invention are WG8=109.22 mm×54.61 mm and WG9A=86.3 6 mm×43.18 mm. It is preferable for the waveguide cavities to be made out of a material that is a good electrical conductor, e.g. aluminium, brass, copper or silver. It may be preferable to use a less expensive and more workable material that has a slightly lower value of conductivity, e.g. aluminium, and then plate the inner cavity walls with a material that has a higher conductivity, e.g. silver. The microwave energy is launched into waveguide cavity 190 using an appropriate microwave connector 180, which may be an N-type or an 7/16"-type, which is connected to a field launch probe or antenna 186 inserted inside waveguide cavity 190 in such a manner that the maximum field from the generator is coupled into waveguide cavity 190. It may be preferable to use an E-field probe or an H-field loop as the field launch probes. It may be preferable to couple the microwave power generator 500 directly into waveguide cavity 190, e.g. the loop coupled output from one of the chambers of a magnetron may be connected directly into waveguide cavity 190 via a quarter wavelength E-field probe or a half wavelength H-field loop. In the instance whereby an E-field probe is used to launch the energy into waveguide cavity 190, it is preferable for the distance between the centre of the probe and the end wall or grill 202 of the waveguide cavity to be an odd multiple of the quarter wavelength at the frequency of operation. In the arrangement shown in FIGS. 21(a) and 21(b), the fog is introduced into the cavity through a hole covered by a mesh or grill 196 located at the underside of the cavity. The grill 196 should contain holes, or slots whose largest dimension is less than or equal to one eighth of the wavelength at the frequency of operation in order to ensure that microwave energy contained within waveguide cavity 190 cannot escape out of the cavity. In the arrangement shown here, the fog is generated using ultrasonic transducer 193 placed inside vessel 192 containing water 191. Ultrasonic transducer 193 may use piezoelectric (PZT) elements to cause vibration of the water molecules to create the fog. The level of water 191 should cover the PZT elements contained within US transducer 193 located at the bottom of vessel 192. This water level may be topped up by inserting a filler pipe 480 into the wall of vessel 192 and connecting the pipe 480 to a water supply. Vessel 192 may include a water level sensor, whose signal is used to control an electronically operated valve to allow the water level to be topped up when it falls below a certain level (this arrangement is not shown here). This invention is not limited to having water vessel 192, ultrasonic transducer 193 and water 191 located on the outside of waveguide cavity 190, i.e. these elements may be located inside waveguide cavity 190. Three tuning stubs or rods 187, 188, 189 are located in the top wall of waveguide 190. These stubs are used to introduce a capacitive or inductive reactance into the cavity and enable any impedance to be set up within waveguide cavity 190. The position of stubs or rods 187, 188, 189 should be such that a high enough electric field is set up within waveguide cavity 190 to create the necessary ionisation discharge needed to produce useful concentrations of OH radicals. This discharge may be assisted by the gas (or gas mixture) fed into waveguide cavity 190 via feed tube 470 and dipole (or electrode) arrangement 197/198 inserted inside waveguide cavity 190.

The gas (or gas mixture) may also be used to create plasma with a spectral content that promotes efficient OH radical generation. The dipole (or electrode) arrangement 197/198 is preferably located at a region within waveguide cavity 190 where the electric field is a maximum—this will be governed by the position of tuning stubs 187, 188, 189. It is preferable for the distance between the centre of first tuning stub 187 and the centre of E-field probe 186 to be an odd multiple of a quarter of the wavelength at the frequency of operation. It is also preferable for the distance between the centres of adjacent tuning stubs to be three eighths of the guide wavelength in order to ensure that any impedance can be set up within waveguide cavity 190. This invention is not limited to these distances, e.g. a quarter guide wavelength, or one eighth guided wavelength may be used for the stub spacing. It is preferable for the dipole arrangement 197/198 to include a pointed monopole needle antenna 197 arrangement with a length equal to a quarter of the wavelength at the frequency of operation and the monopole 197 should be located at the centre of a circular plate or disk 198 with a diameter equal to a half the wavelength at the frequency of operation. This invention is not limited to using a dipole arrangement to assist with the creation of ionisation discharges, i.e. other antenna structures or stubs located inside the waveguide cavity may be used.

The input and output faces of waveguide cavity 190 are covered with a wire mesh or grid or metal sheet, with holes drilled in them or slots milled in them, 202 and 195 respectively, whose largest dimension (diameter or length) should be less than or equal to one eighth of the wavelength at the frequency of operation in order to ensure that microwave energy contained within waveguide cavity 190 cannot escape out of the cavity. A fan (or plurality of fans) 201, 194 are connected to the outside of wire meshes or grids or metal sheets with holes drilled in them or slots milled in them 202 and 195 to enable the OH radicals 303 to be blown through and extracted from waveguide cavity 190 and blown into the open or enclosed space that needs to be disinfected or sterilised.

In the arrangement shown in FIGS. 21(*a*) and 21(*b*), a hollow pipe or tube or rectangular waveguide section with two bends 203 is connected between the output fan 194 and the input fan 201 to blow a portion of the OH radicals produced at the output of the device, together with a volume of air, back into the system to enable the OH radicals to be blown through waveguide cavity 190 in an efficient manner. The arrangement shows first fan 201 totally covered by pipe 203 and second fan 194 only partially covered so as to allow the OH radicals 303 to be drawn out into the space that requires disinfection, bug kill, bacteria kill or sterilisation. It may be preferable to only cover a section of first fan 201 to allow a greater volume of air to enter waveguide cavity 190. It may be preferable to remove pipe 203 and it may be preferable to remove one of the two fans (or arrangements of fans) 201, 194.

Figures 22A, 22B:
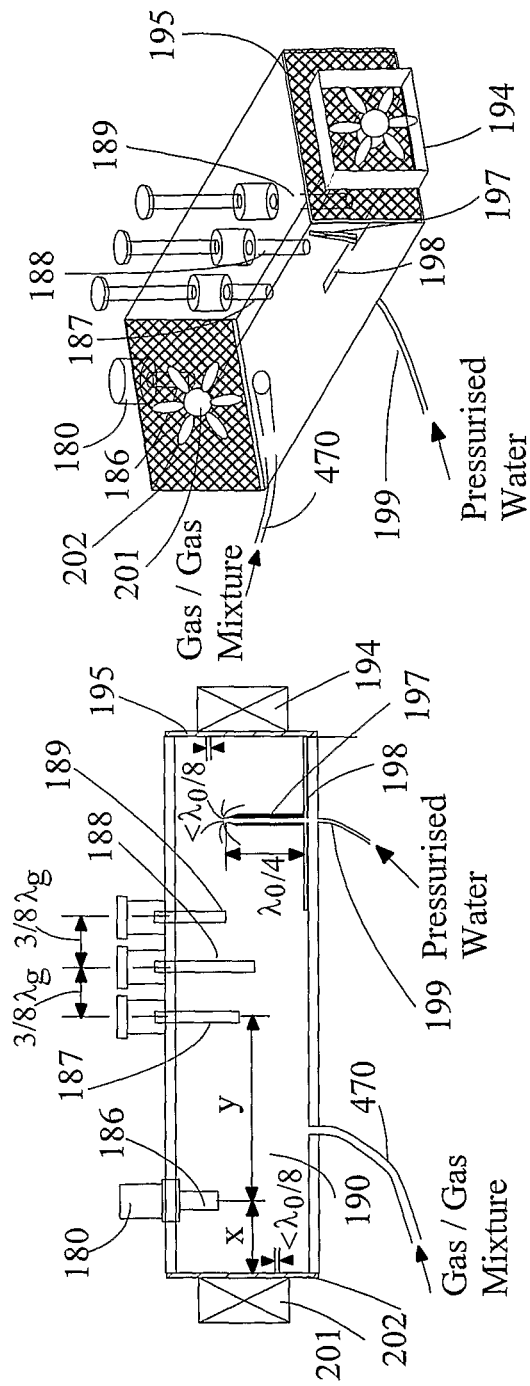
FIGS. 22(*a*) and 22(*b*) are views of a second plasma applicator according to another embodiment of the invention.

FIGS. 22(*a*) and 22(*b*) show a similar arrangement to that shown in FIGS. 21(*a*) and 21(*b*) except that the arrangement used to introduce fog into the cavity (ultrasonic transducer 193, water vessel 192, water 191 and hole and mesh in bottom of waveguide 196) has been replaced by a slot or hole made in needle antenna or monopole 197 and a supply of pressurised water used to create a mist at the end of monopole 197, which is used to create the OH radicals from the ionisation discharge caused by the overall dipole antenna 197/198, the position of tuning stubs 187, 188, 189 and the gas (or gas mixture). The pressurised water is fed into waveguide cavity 190 via feed pipe 199 and a small hole drilled into the bottom of waveguide cavity 190. In this arrangement, recycling pipe 203 has been removed.

Figures 23A, 23B:
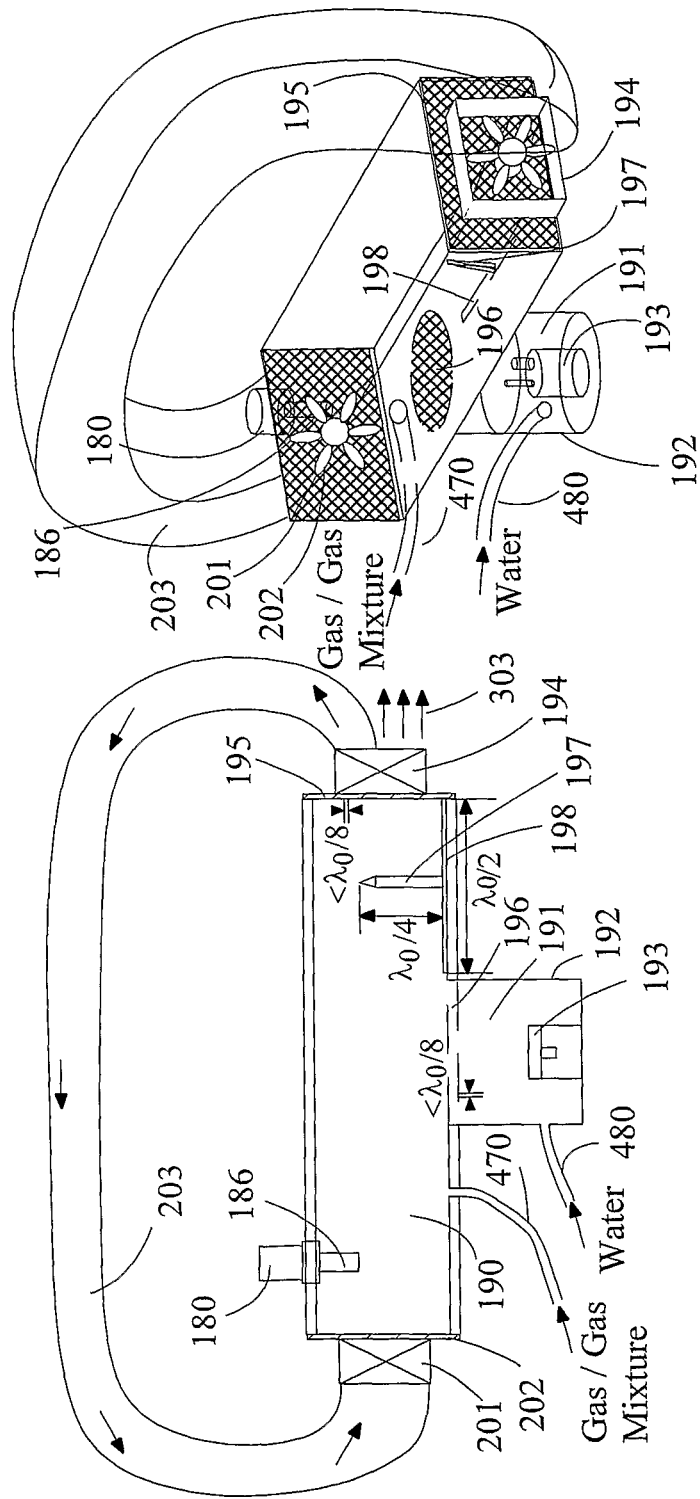
FIGS. 23(*a*) and 23(*b*) are views of a third plasma applicator according to yet another embodiment of the invention.

FIGS. 23(*a*) and 23(*b*) show a similar arrangement to that shown in FIGS. 21(*a*) and 21(*b*) except that the tuning stubs 187, 188, 189 have been removed from waveguide cavity 190 and the ionisation discharge is created solely by the dipole arrangement 197/198 (or similar) and the gas (or gas mixes) that fills waveguide cavity 190. This arrangement includes recycling pipe 203 with a first fan 201 to blow air and radicals through the system and a second fan 194 to extract the radicals from the system into the portable enclosure.

Figures 24A, 24B:
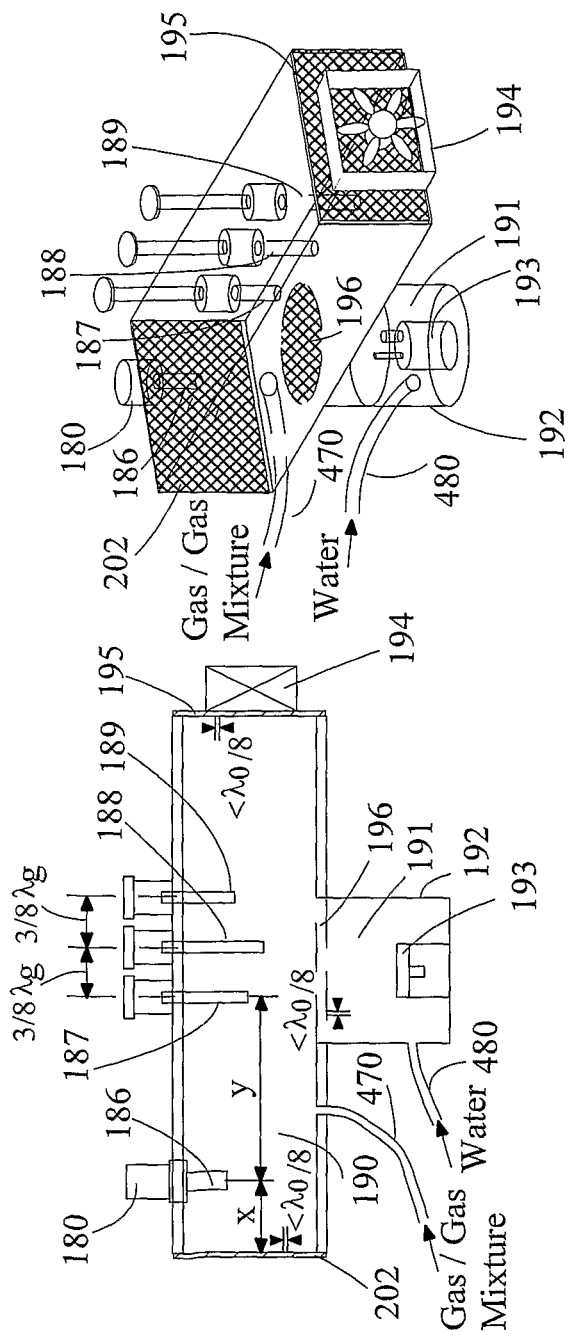
FIGS. 24(*a*) and 24(*b*) are views of a fourth plasma applicator according to yet another embodiment of the invention.

FIGS. 24(*a*) and 24(*b*) show a similar arrangement to that shown in FIGS. 21(*a*) and 21(*b*) except that the dipole arrangement 197/198 (or similar) has been removed and the ionisation discharges are caused by the position of the tuning stubs 187, 188, 189 within waveguide cavity 190 and the gas (or gas mixes) that fill waveguide cavity 190. In this arrangement, first fan 201 and recycling pipe 203 have also been removed.

FIGS. 25(*a*) and 25(*b*) show a similar arrangement to that shown in FIGS. 21(*a*) and 21(*b*) except that tuning stubs 187, 188, 189 have been removed from waveguide cavity 190 and the ionisation discharge is created solely by the dipole arrangement 197/198 (or similar) and the gas (or gas mixes) that fill waveguide cavity 190. Also that the arrangement used to introduce fog into the cavity (US transducer 193, water vessel 192, water 191 and hole and mesh in bottom of waveguide 196) has been replaced by a slot or hole made in needle antenna or monopole 197 and a supply of pressurised water is used to create a mist at the end of the monopole 197, which is used to create the OH radicals from the ionisation discharge created by the overall dipole antenna 197/198, the gas (or gas mixture) and the microwave power. The pressurised water is fed into waveguide cavity 190 via feed pipe 199, which enters waveguide cavity 190 through a small hole drilled in the bottom of the waveguide. In this arrangement, first fan 201, first wire mesh 202 and recycling pipe 203 have also been removed.

It is preferable for tuning stubs 187, 188, 189, wire meshes or grids 195, 196, 202 and dipole arrangement 197/198 to be made from a metallic material that has a high electrical conductivity, i.e. copper, aluminium, brass or silver.

It may be noted that the height (length of short wall) of waveguide 190 may be varied over lengths equal to an odd multiple of the wavelength at the frequency of operation to form quarter wavelength transformer sections in waveguide rather than in a coaxial arrangement that supports a TEM wave. These waveguide transformers may be used to create a high local electric field at the end of the applicator to produce ionisation discharges.

This invention may be used to address the following applications: hospital ward or bed-space sterilisation, sterilisation or decontamination of isolated sections of operating theatres, sterilisation or disinfection of residential care homes, sterilisation of disinfection of offices, doctor, dental, veterinary surgeries and private homes, disinfection or cleaning of carpets and flooring materials, wound bed sterilisation, hospital equipment (beds, tables, chairs, sets of drawers, curtains, instruments, clip-boards, pens) sterilisation, internal tissue or biological insert sterilisation, treatment of sexually transmitted diseases, treatment of ulcers or bed sores, treatment of water, treatment of airborne germs or viruses in operating theatres or rooms associated with operating theatres, treatment of athletes foot, or treatment of alopecia aerate. This invention is not limited to these particular applications.

The invention claimed is:

1. Sterilisation apparatus comprising
    an applicator having a hydroxyl radical generating region and an outlet for directing generated hydroxyl radicals out of the hydroxyl radical generating region towards a region to be sterilised;
    an enclosure for confining the hydroxyl radicals in the region to be sterilised;
    a power generator connected to deliver microwave or RF energy into the hydroxyl radical generating region; and
    a mist generator connected to deliver water mist into the hydroxyl radical generating region,
    wherein the applicator comprises a coaxial assembly connected to the power generator for receiving the microwave or RF energy, the coaxial assembly having:
    an outer conductor,
    an inner conductor surrounded by and separated from the outer conductor, the inner conductor comprising a hollow portion having a nozzle located at the distal end of the inner conductor, and
    a feed pipe connected to a water source for supplying water to the hollow portion for delivery as water mist through the nozzle to the hydroxyl radical generating region, and
    wherein the inner conductor tapers at its distal end and is configured to create a high impedance at the hydroxyl radical generating region and to concentrate the received microwave or RF energy into an electric field in the hydroxyl radical generating region when water mist and the microwave or RF energy are delivered thereto thereby to create an ionisation discharge for generating hydroxyl radicals for delivery out of the applicator.

2. Sterilisation apparatus according to claim 1 including a gas feed pipe for supplying gas to the hollow portion for delivery through the nozzle into the hydroxyl radical generating region, wherein the created ionisation discharge is a plasma of the gas.

3. Sterilisation apparatus according to claim 1, wherein the power generator is a microwave radiation generator and comprises a controller arranged adjustably to control the microwave energy delivered to the hydroxyl radical generating region.

4. Sterilisation apparatus according to claim 3, wherein the controller includes a modulator arranged to pulse the microwave energy whereby the ionisation discharge is created by the leading edge of each pulse.

5. Sterilisation apparatus according to claim 1, wherein the mist generator includes a valve contained within the hollow portion of the inner conductor of the coaxial assembly, the valve having an outlet located to deliver mist to the nozzle at the distal end of the inner conductor.

6. Sterilisation apparatus according to claim 5, wherein the valve is a needle valve comprising a solenoid.

7. Sterilisation apparatus according to claim 1, wherein the coaxial assembly includes a plurality of quarter wave transformers each having a different impedance, the plurality of quarter wave transformers being arranged to concentrate an electric field in the hydroxyl radical generating region.

8. Sterilisation apparatus according to claim 3, wherein the microwave radiation generator includes an amplifier and the controller includes a variable attenuator arranged to control a power level of a signal input to the amplifier.

9. Sterilisation apparatus according claim 8, wherein the controller includes an amplifier signal modulator arranged to modulate an activation signal for the amplifier.

10. Sterilisation apparatus according to claim 1, wherein the power generator is arranged to generate RF energy.

11. Sterilisation apparatus according to claim 1 including an impedance adjustor arranged to control the impedance at the hydroxyl radical generating region when water mist and energy are delivered thereto.

12. Sterilisation apparatus according to claim 11, including a reflected signal detector arranged to detect energy reflected back from the hydroxyl radical generating region, wherein the reflected signal detector is connected to a controller that is arranged to operate the impedance adjustor based on information concerning detected reflected microwave energy from the reflected signal detector.

13. Plasma sterilisation apparatus according to claim 12 including a forward signal detector arranged to detect energy delivered to the hydroxyl radical generating region, wherein the forward signal detector is connected to the controller and the controller is arranged to adjustably control the energy delivered to the hydroxyl radical generating region based on information concerning detected forward and reflected microwave energy from the forward and reflected signal detectors respectively.

14. Plasma sterilisation apparatus according to claim 1, wherein the enclosure seals the region to be sterilised.

15. Plasma sterilisation apparatus according to claim 1, wherein the enclosure comprises a flexible tent.

16. The plasma sterilization apparatus of claim 8, wherein the variable attenuator is a PIN diode attenuator.

* * * * *